United States Patent
Martucci et al.

(10) Patent No.: US 6,985,870 B2
(45) Date of Patent: Jan. 10, 2006

(54) MEDICATION DELIVERY SYSTEM

(75) Inventors: James Martucci, Libertyville, IL (US); Tuan Bui, Green Oaks, IL (US); James Hitchcock, Barrington, IL (US); Aleandro DiGianfilippo, Scottsdale, AZ (US); Richard Pierce, Glendale, AZ (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 10/043,891

(22) Filed: Jan. 11, 2002

(65) Prior Publication Data

US 2003/0135388 A1 Jul. 17, 2003

(51) Int. Cl.
| | |
|---|---|
| G06F 17/60 | (2006.01) |
| G06F 7/08 | (2006.01) |
| G06G 17/00 | (2006.01) |
| A61M 31/00 | (2006.01) |
| A61M 5/00 | (2006.01) |

(52) U.S. Cl. ............................. 705/3; 604/65; 604/246; 705/2; 705/22; 705/28; 235/375; 235/381

(58) Field of Classification Search ................ 604/65, 604/123, 246, 83, 151; 235/375, 462.45, 235/472.01, 382, 462.03, 494; 705/2–4, 22, 705/28; 700/213–237, 282; 222/81; 141/330–367; 340/825.49, 573.4

See application file for complete search history.

(56) References Cited

U.S. PATENT DOCUMENTS

| | | |
|---|---|---|
| 3,564,172 A | 2/1971 | Laakso |
| 3,809,871 A | 5/1974 | Howard et al. |
| 3,848,112 A | 11/1974 | Weichselbaum et al. |

(Continued)

FOREIGN PATENT DOCUMENTS

| | | |
|---|---|---|
| CN | 155687 | 4/1991 |
| DE | 3709857 A1 | 10/1988 |
| DE | 3812584 A1 | 10/1989 |

(Continued)

OTHER PUBLICATIONS

Perlstein, P.H., Edwards, N.K., Atherton, H.D., Sutherland, J.M., "Computer–Assisted Newborn Intensive Care," *Pediatrics*, Apr. 1976, pp. 494–501, vol.. 57 No. 4.

(Continued)

*Primary Examiner*—Nicholas D. Lucchesi
*Assistant Examiner*—Roz Maiorino
(74) *Attorney, Agent, or Firm*—Bell Boyd & Lloyd LLC

(57) ABSTRACT

A medication delivery system (20) having features of the present invention comprises a medical container (26) holding a prescribed medication (27) to be delivered to a patient, a tag 24 adapted to be worn by the patient, a handheld computing device (22), and an electronic medication delivery device (30). Data on the medication (27) is contained in a first label (28) on the medication container (27). The first label (28) also contains the instruction on how the medication is delivered to the patient, including the appropriate settings for an electronic medication delivery device for delivering the medication to the patient. Patient data is contained in a second label (29) on the tag (24) worn by the patient. The medication data, medication delivery instruction, and patient data are provided in machine readable formats. The handheld computing device (22) reads the medication data and the medication delivery instruction on the medication container (26) and the patient data on the patient tag (24). The handheld computing device (22) stores the information obtained and performs a matching check to confirm that the medication data matches with the patient data. Upon a confirmed match, it transmits the medication delivery instruction to the electronic medication delivery device (30), which downloads the instruction, programs the delivery device 30, and prompts an operator to begin delivering the medication (27) to the patient according to the downloaded instruction.

58 Claims, 32 Drawing Sheets

U.S. PATENT DOCUMENTS

| | | |
|---|---|---|
| 3,921,196 A | 11/1975 | Patterson |
| 3,923,364 A | 12/1975 | Shapiro et al. |
| 4,032,908 A | 6/1977 | Rice et al. |
| 4,126,132 A | 11/1978 | Portner et al. |
| 4,151,407 A | 4/1979 | McBride et al. |
| 4,164,320 A | 8/1979 | Irazoqui et al. |
| 4,270,532 A | 6/1981 | Franetzki et al. |
| 4,282,872 A | 8/1981 | Franetzki et al. |
| 4,308,866 A | 1/1982 | Jelliffe et al. |
| 4,373,527 A | 2/1983 | Fischell |
| 4,457,750 A | 7/1984 | Hill |
| 4,464,172 A | 8/1984 | Lichtenstein |
| 4,469,481 A | 9/1984 | Kobayashi |
| 4,476,381 A | 10/1984 | Rubin |
| 4,510,489 A | 4/1985 | Anderson, III et al. |
| 4,510,490 A | 4/1985 | Anderson, III et al. |
| 4,526,404 A | 7/1985 | Vasquez |
| 4,529,401 A | 7/1985 | Leslie et al. |
| 4,538,138 A | 8/1985 | Harvey et al. |
| 4,560,979 A | 12/1985 | Rosskopf |
| 4,573,994 A | 3/1986 | Fischell et al. |
| 4,619,653 A | 10/1986 | Fischell |
| 4,624,661 A | 11/1986 | Arimond |
| 4,628,193 A | 12/1986 | Blum |
| 4,636,950 A | 1/1987 | Caswell et al. |
| 4,681,563 A | 7/1987 | Deckert et al. |
| 4,696,671 A | 9/1987 | Epstein et al. |
| 4,697,928 A | 10/1987 | Csongor |
| 4,705,506 A | 11/1987 | Archibald |
| 4,717,042 A | 1/1988 | McLaughlin |
| 4,722,734 A | 2/1988 | Kolln |
| 4,730,849 A | 3/1988 | Siegel |
| 4,731,051 A | 3/1988 | Fischell |
| 4,732,411 A | 3/1988 | Siegel |
| 4,741,732 A | 5/1988 | Crankshaw et al. |
| 4,741,736 A | 5/1988 | Brown |
| 4,756,706 A | 7/1988 | Kerns et al. |
| D297,939 S | 10/1988 | Bradbury et al. |
| 4,778,449 A | 10/1988 | Weber et al. |
| 4,784,645 A | 11/1988 | Fischell |
| 4,785,969 A | 11/1988 | McLaughlin |
| 4,803,625 A | 2/1989 | Fu et al. |
| 4,810,243 A | 3/1989 | Howson |
| 4,811,844 A | 3/1989 | Moulding, Jr. et al. |
| 4,814,759 A | 3/1989 | Gombrich et al. |
| 4,816,208 A | 3/1989 | Woods et al. |
| 4,817,044 A | 3/1989 | Ogren |
| 4,818,850 A | 4/1989 | Gombrich et al. |
| 4,828,545 A | 5/1989 | Epstein et al. |
| 4,831,562 A | 5/1989 | McIntosh et al. |
| 4,835,372 A | 5/1989 | Gombrich et al. |
| 4,835,521 A | 5/1989 | Andrejasich et al. |
| 4,839,806 A | 6/1989 | Goldfischer et al. |
| 4,847,764 A | 7/1989 | Halvorson |
| 4,850,009 A | 7/1989 | Zook et al. |
| 4,853,521 A | 8/1989 | Claeys et al. |
| 4,857,713 A | 8/1989 | Brown |
| 4,857,716 A | 8/1989 | Gombrich et al. |
| 4,865,584 A | 9/1989 | Epstein et al. |
| 4,871,351 A | 10/1989 | Feingold |
| 4,878,175 A | 10/1989 | Norden-Paul et al. |
| 4,886,495 A | 12/1989 | Reynolds |
| 4,893,270 A | 1/1990 | Beck et al. |
| 4,898,576 A | 2/1990 | Philip |
| 4,898,578 A | 2/1990 | Rubalcaba, Jr. |
| 4,916,441 A | 4/1990 | Gombrich |
| 4,925,444 A | 5/1990 | Orkin et al. |
| 4,939,508 A | 7/1990 | Lawrence et al. |
| 4,943,279 A | 7/1990 | Samiotes et al. |
| 4,951,029 A | 8/1990 | Severson |
| 4,967,928 A | 11/1990 | Carter |
| 4,977,590 A | 12/1990 | Milovancevic |
| 4,978,335 A | 12/1990 | Arthur, III |
| 4,991,091 A | 2/1991 | Allen |
| 4,998,249 A | 3/1991 | Bennett et al. |
| 5,002,055 A | 3/1991 | Merki et al. |
| 5,006,699 A | 4/1991 | Felkner et al. |
| 5,014,875 A | 5/1991 | McLaughlin et al. |
| 5,016,172 A | 5/1991 | Dessertine |
| 5,034,004 A | 7/1991 | Crankshaw |
| 5,036,852 A | 8/1991 | Leishman |
| 5,041,086 A | 8/1991 | Koenig et al. |
| 5,053,774 A | 10/1991 | Schuermann et al. |
| 5,072,383 A | 12/1991 | Brimm et al. |
| 5,077,666 A | 12/1991 | Brimm et al. |
| 5,078,683 A | 1/1992 | Sancoff et al. |
| 5,084,828 A | 1/1992 | Kaufman et al. |
| 5,087,245 A | 2/1992 | Doan |
| 5,088,981 A | 2/1992 | Howson et al. |
| 5,096,385 A | 3/1992 | Georgi et al. |
| 5,100,380 A | 3/1992 | Epstein et al. |
| 5,108,367 A | 4/1992 | Epstein et al. |
| 5,131,816 A | 7/1992 | Brown et al. |
| 5,153,416 A | 10/1992 | Neeley |
| 5,153,827 A | 10/1992 | Coutré et al. |
| 5,158,091 A | 10/1992 | Butterfield et al. |
| 5,179,569 A | 1/1993 | Sawyer |
| 5,181,910 A | 1/1993 | Scanlon |
| 5,195,522 A | 3/1993 | Pytel et al. |
| 5,201,725 A | 4/1993 | Kling |
| 5,207,642 A | 5/1993 | Orkin et al. |
| 5,208,907 A | 5/1993 | Shelton et al. |
| 5,213,232 A | 5/1993 | Kraft et al. |
| 5,216,760 A | 6/1993 | Brown et al. |
| 5,240,007 A | 8/1993 | Pytel et al. |
| 5,242,408 A | 9/1993 | Jhuboo et al. |
| 5,242,432 A | 9/1993 | DeFrank |
| 5,244,463 A | 9/1993 | Cordner, Jr. et al. |
| 5,247,611 A | 9/1993 | Norden-Paul et al. |
| 5,253,361 A | 10/1993 | Thurman et al. |
| 5,253,362 A | 10/1993 | Nolan et al. |
| 5,254,096 A | 10/1993 | Rondelet et al. |
| 5,256,157 A | 10/1993 | Samiotes et al. |
| 5,265,010 A | 11/1993 | Evans-Paganelli et al. |
| 5,267,174 A | 11/1993 | Kaufman et al. |
| 5,271,405 A | 12/1993 | Boyer et al. |
| 5,272,318 A | 12/1993 | Gorman |
| 5,272,321 A | 12/1993 | Otsuka et al. |
| 5,284,150 A | 2/1994 | Butterfield et al. |
| 5,291,399 A | 3/1994 | Chaco |
| 5,292,029 A | 3/1994 | Pearson |
| 5,300,111 A | 4/1994 | Panton et al. |
| 5,301,105 A | 4/1994 | Cummings, Jr. |
| 5,301,319 A | 4/1994 | Thurman et al. |
| 5,307,372 A | 4/1994 | Sawyer et al. |
| 5,307,463 A | 4/1994 | Hyatt et al. |
| 5,314,243 A | 5/1994 | McDonald et al. |
| 5,315,505 A | 5/1994 | Pratt et al. |
| 5,317,506 A | 5/1994 | Coutrés et al. |
| 5,319,543 A | 6/1994 | Wilhelm |
| 5,324,422 A | 6/1994 | Colleran et al. |
| 5,325,478 A | 6/1994 | Shelton et al. |
| 5,338,157 A | 8/1994 | Blomquist |
| 5,341,412 A | 8/1994 | Ramot et al. |
| 5,356,378 A | 10/1994 | Doan |
| 5,367,555 A | 11/1994 | Isoyama |
| 5,368,562 A | 11/1994 | Blomquist et al. |
| 5,371,687 A | 12/1994 | Holmes, II et al. |
| 5,374,813 A | 12/1994 | Shipp |
| 5,376,070 A | 12/1994 | Purvis et al. |
| 5,378,231 A | 1/1995 | Johnson et al. |
| 5,383,858 A | 1/1995 | Reilly et al. |
| 5,390,238 A | 2/1995 | Kirk et al. |
| 5,395,320 A | 3/1995 | Padda et al. |
| 5,401,059 A | 3/1995 | Ferrario |
| 5,404,292 A | 4/1995 | Hendrickson |
| 5,404,384 A | 4/1995 | Colburn et al. |
| 5,412,715 A | 5/1995 | Volpe |
| 5,413,111 A | 5/1995 | Wilkinson |
| 5,416,695 A | 5/1995 | Stutman et al. |

| | | |
|---|---|---|
| 5,417,222 A | 5/1995 | Dempsey et al. |
| 5,429,401 A | 7/1995 | Youmans |
| 5,429,602 A | 7/1995 | Hauser |
| 5,431,299 A | 7/1995 | Brewer et al. |
| 5,445,294 A | 8/1995 | Gardner et al. |
| 5,445,621 A | 8/1995 | Poli et al. |
| 5,453,098 A | 9/1995 | Botts et al. |
| 5,455,851 A | 10/1995 | Chaco et al. |
| 5,458,123 A | 10/1995 | Unger |
| 5,460,294 A | 10/1995 | Williams |
| 5,461,665 A | 10/1995 | Shur et al. |
| 5,465,082 A * | 11/1995 | Chaco .................. 340/825.49 |
| 5,465,286 A | 11/1995 | Clare et al. |
| 5,468,110 A | 11/1995 | McDonald et al. |
| 5,471,382 A | 11/1995 | Tallman et al. |
| 5,485,408 A | 1/1996 | Blomquist |
| 5,490,610 A | 2/1996 | Pearson |
| 5,495,961 A | 3/1996 | Maestre |
| 5,502,944 A | 4/1996 | Kraft et al. |
| 5,507,412 A | 4/1996 | Ebert et al. |
| 5,511,951 A | 4/1996 | O'Leary |
| 5,515,426 A | 5/1996 | Yacenda et al. |
| 5,520,450 A | 5/1996 | Colson, Jr. et al. |
| 5,529,063 A | 6/1996 | Hill |
| 5,531,697 A | 7/1996 | Olsen et al. |
| 5,531,698 A | 7/1996 | Olsen |
| 5,533,079 A | 7/1996 | Colburn et al. |
| 5,534,691 A | 7/1996 | Holdaway et al. |
| 5,536,084 A | 7/1996 | Curtis et al. |
| 5,537,313 A | 7/1996 | Pirelli |
| 5,537,853 A | 7/1996 | Finburgh et al. |
| 5,539,836 A | 7/1996 | Babkin |
| 5,542,420 A | 8/1996 | Goldman et al. |
| 5,542,826 A | 8/1996 | Warner |
| 5,547,470 A | 8/1996 | Johnson et al. |
| 5,558,638 A | 9/1996 | Evers et al. |
| 5,558,640 A | 9/1996 | Pfeiler et al. |
| 5,560,352 A | 10/1996 | Heim et al. |
| 5,562,232 A | 10/1996 | Pearson |
| 5,562,621 A | 10/1996 | Claude et al. |
| 5,563,347 A | 10/1996 | Martin et al. |
| 5,564,803 A | 10/1996 | McDonald et al. |
| 5,568,912 A | 10/1996 | Minami et al. |
| 5,569,186 A | 10/1996 | Lord et al. |
| 5,569,187 A | 10/1996 | Kaiser |
| 5,571,258 A | 11/1996 | Pearson |
| 5,573,506 A | 11/1996 | Vasko |
| 5,575,632 A | 11/1996 | Morris et al. |
| 5,581,687 A | 12/1996 | Lyle et al. |
| 5,582,593 A | 12/1996 | Hultman |
| 5,590,648 A | 1/1997 | Mitchell et al. |
| 5,593,267 A | 1/1997 | McDonald et al. |
| 5,594,786 A | 1/1997 | Chaco et al. |
| 5,597,995 A | 1/1997 | Williams et al. |
| 5,598,838 A | 2/1997 | Servidio et al. |
| 5,601,420 A | 2/1997 | Warner et al. |
| 5,602,961 A | 2/1997 | Kolesnik et al. |
| 5,603,613 A | 2/1997 | Butterfield et al. |
| 5,609,576 A | 3/1997 | Voss et al. |
| 5,612,869 A | 3/1997 | Letzt et al. |
| 5,630,710 A | 5/1997 | Tune et al. |
| 5,640,301 A | 6/1997 | Roecker et al. |
| 5,641,892 A | 6/1997 | Larkins et al. |
| 5,642,438 A | 6/1997 | Babkin |
| 5,643,212 A | 7/1997 | Coutré et al. |
| 5,647,854 A | 7/1997 | Olsen et al. |
| 5,651,775 A | 7/1997 | Walker et al. |
| 5,658,250 A | 8/1997 | Blomquist et al. |
| 5,659,659 A | 8/1997 | Kolesnik et al. |
| 5,661,978 A | 9/1997 | Holmes et al. |
| D384,578 S | 10/1997 | Wangu et al. |
| 5,676,346 A | 10/1997 | Leinsing |
| 5,681,285 A | 10/1997 | Ford et al. |
| 5,683,367 A | 11/1997 | Jordan et al. |
| 5,689,229 A | 11/1997 | Chaco et al. |
| 5,697,899 A | 12/1997 | Hillman et al. |
| 5,697,951 A | 12/1997 | Harpstead et al. |
| 5,700,998 A * | 12/1997 | Palti .......................... 235/375 |
| 5,712,795 A | 1/1998 | Layman et al. |
| 5,713,485 A | 2/1998 | Liff et al. |
| 5,713,856 A | 2/1998 | Eggers et al. |
| 5,713,865 A | 2/1998 | Manning et al. |
| 5,716,114 A | 2/1998 | Holmes et al. |
| 5,716,194 A | 2/1998 | Butterfield et al. |
| 5,718,562 A | 2/1998 | Lawless et al. |
| 5,719,761 A | 2/1998 | Gatti et al. |
| RE35,743 E | 3/1998 | Pearson |
| 5,722,947 A | 3/1998 | Jeppsson et al. |
| 5,724,580 A | 3/1998 | Levin et al. |
| 5,729,655 A | 3/1998 | Kolesnik et al. |
| 5,738,102 A | 4/1998 | Lemelson |
| 5,741,121 A | 4/1998 | O'Leary |
| 5,755,683 A | 5/1998 | Houle et al. |
| 5,764,923 A | 6/1998 | Tallman et al. |
| 5,769,811 A | 6/1998 | Stacey et al. |
| 5,772,585 A | 6/1998 | Lavin et al. |
| 5,772,635 A | 6/1998 | Dastur et al. |
| 5,772,637 A | 6/1998 | Heinzmann et al. |
| 5,776,057 A | 7/1998 | Swenson et al. |
| 5,781,442 A | 7/1998 | Engleson et al. |
| 5,788,669 A | 8/1998 | Peterson |
| 5,790,409 A | 8/1998 | Fedor et al. |
| 5,793,861 A | 8/1998 | Haigh |
| 5,795,327 A | 8/1998 | Wilson et al. |
| 5,797,515 A | 8/1998 | Liff et al. |
| 5,800,387 A | 9/1998 | Duffy et al. |
| 5,803,906 A | 9/1998 | Pratt et al. |
| 5,803,917 A | 9/1998 | Butterfield et al. |
| 5,807,336 A | 9/1998 | Russo et al. |
| 5,813,972 A | 9/1998 | Nazarian et al. |
| 5,814,015 A | 9/1998 | Gargano et al. |
| 5,815,566 A | 9/1998 | Ramot et al. |
| 5,818,535 A | 10/1998 | Asnis et al. |
| 5,822,418 A | 10/1998 | Yacenda et al. |
| 5,822,544 A | 10/1998 | Chaco et al. |
| 5,823,949 A | 10/1998 | Goltra |
| 5,826,621 A | 10/1998 | Jemmott |
| 5,827,180 A | 10/1998 | Goodman |
| 5,827,223 A | 10/1998 | Butterfield |
| 5,832,443 A | 11/1998 | Kolesnik et al. |
| 5,833,599 A | 11/1998 | Schrier et al. |
| 5,836,910 A | 11/1998 | Duffy et al. |
| 5,839,715 A | 11/1998 | Leinsing |
| 5,841,975 A | 11/1998 | Layne et al. |
| 5,842,976 A | 12/1998 | Williamson |
| 5,848,593 A | 12/1998 | McGrady et al. |
| 5,848,988 A | 12/1998 | Davis |
| 5,852,590 A | 12/1998 | de la Huerga |
| 5,853,386 A | 12/1998 | Davis et al. |
| 5,855,550 A | 1/1999 | Lai et al. |
| 5,865,745 A | 2/1999 | Schmitt et al. |
| 5,865,813 A | 2/1999 | DeKalb et al. |
| 5,867,821 A | 2/1999 | Ballantyne et al. |
| 5,871,465 A | 2/1999 | Vasko |
| 5,878,885 A | 3/1999 | Wangu et al. |
| 5,880,443 A | 3/1999 | McDonald et al. |
| 5,883,576 A | 3/1999 | De La Huerga |
| 5,893,697 A | 4/1999 | Zini et al. |
| 5,895,371 A | 4/1999 | Levitas et al. |
| 5,895,461 A | 4/1999 | De La Huerga et al. |
| 5,897,493 A | 4/1999 | Brown |
| 5,899,665 A | 5/1999 | Makino et al. |
| 5,903,889 A | 5/1999 | de la Huerga et al. |
| 5,907,291 A | 5/1999 | Chen et al. |
| 5,908,027 A | 6/1999 | Butterfield et al. |
| 5,910,107 A | 6/1999 | Iliff |
| 5,911,132 A | 6/1999 | Sloane |
| 5,912,818 A | 6/1999 | McGrady et al. |
| 5,913,197 A | 6/1999 | Kameda |
| 5,913,310 A | 6/1999 | Brown |
| 5,915,240 A | 6/1999 | Karpf |
| 5,923,018 A | 7/1999 | Kameda et al. |

| Patent No. | Date | Inventor |
|---|---|---|
| 5,924,074 A | 7/1999 | Evans |
| 5,924,103 A | 7/1999 | Ahmed et al. |
| 5,927,274 A | 7/1999 | Servidio et al. |
| 5,935,099 A | 8/1999 | Peterson et al. |
| 5,938,413 A | 8/1999 | Makino et al. |
| 5,939,699 A | 8/1999 | Perttunen et al. |
| 5,940,306 A | 8/1999 | Gardner et al. |
| 5,941,846 A | 8/1999 | Duffy et al. |
| 5,943,633 A | 8/1999 | Wilson et al. |
| 5,945,651 A | 8/1999 | Chorosinski et al. |
| 5,946,659 A | 8/1999 | Lancelot et al. |
| 5,956,023 A | 9/1999 | Lyle et al. |
| 5,957,885 A | 9/1999 | Bollish et al. |
| 5,960,085 A | 9/1999 | de la Huerga |
| 5,961,448 A | 10/1999 | Swenson et al. |
| 5,961,487 A | 10/1999 | Davis |
| 5,964,700 A | 10/1999 | Tallman et al. |
| 5,967,484 A | 10/1999 | Morris |
| 5,971,593 A | 10/1999 | McGrady |
| 5,980,501 A | 11/1999 | Gray |
| 5,993,046 A | 11/1999 | McGrady et al. |
| 5,995,939 A | 11/1999 | Berman et al. |
| 5,995,965 A | 11/1999 | Experton |
| 5,997,476 A | 12/1999 | Brown |
| 5,997,617 A | 12/1999 | Czabala et al. |
| 6,003,006 A | 12/1999 | Colella et al. |
| 6,009,333 A | 12/1999 | Chaco |
| 6,016,044 A | 1/2000 | Holdaway |
| 6,017,318 A | 1/2000 | Gauthier et al. |
| 6,018,713 A | 1/2000 | Coli et al. |
| 6,019,745 A | 2/2000 | Gray |
| 6,021,392 A * | 2/2000 | Lester et al. .................. 705/2 |
| 6,024,539 A | 2/2000 | Blomquist |
| 6,029,946 A | 2/2000 | Doyle |
| 6,032,155 A | 2/2000 | de la Huerga |
| 6,036,171 A | 3/2000 | Weinheimer et al. |
| 6,044,134 A | 3/2000 | De La Huerga |
| 6,065,819 A | 5/2000 | Holmes et al. |
| 6,068,156 A | 5/2000 | Liff et al. |
| 6,070,761 A * | 6/2000 | Bloom et al. ................. 222/81 |
| 6,074,345 A | 6/2000 | van Oostrom et al. |
| 6,082,776 A | 7/2000 | Feinberg |
| 6,089,541 A | 7/2000 | Weinheimer et al. |
| 6,093,146 A | 7/2000 | Filangeri |
| 6,101,478 A | 8/2000 | Brown |
| 6,108,588 A | 8/2000 | McGrady |
| 6,109,774 A | 8/2000 | Holmes et al. |
| 6,110,153 A | 8/2000 | Davis et al. |
| 6,116,461 A | 9/2000 | Broadfield et al. |
| 6,119,694 A | 9/2000 | Correa et al. |
| 6,123,686 A | 9/2000 | Olsen et al. |
| 6,139,495 A | 10/2000 | De La Huerga |
| 6,142,446 A | 11/2000 | Leinsing |
| 6,146,109 A | 11/2000 | Davis et al. |
| 6,148,339 A | 11/2000 | Nagamatsu et al. |
| 6,152,364 A | 11/2000 | Schoonen et al. |
| 6,154,726 A | 11/2000 | Rensimer et al. |
| 6,157,914 A | 12/2000 | Seto et al. |
| 6,158,965 A | 12/2000 | Butterfield et al. |
| 6,160,478 A | 12/2000 | Jacobsen et al. |
| 6,161,095 A | 12/2000 | Brown |
| 6,163,737 A | 12/2000 | Fedor et al. |
| 6,165,154 A | 12/2000 | Gray et al. |
| 6,170,007 B1 | 1/2001 | Venkatraman et al. |
| 6,170,746 B1 | 1/2001 | Brook et al. |
| 6,171,264 B1 | 1/2001 | Bader |
| 6,175,779 B1 | 1/2001 | Barrett |
| 6,186,145 B1 | 2/2001 | Brown |
| 6,190,441 B1 | 2/2001 | Czabala et al. |
| 6,193,480 B1 | 2/2001 | Butterfield |
| 6,206,829 B1 | 3/2001 | Iliff |
| 6,210,361 B1 | 4/2001 | Kamen et al. |
| 6,211,642 B1 | 4/2001 | Holdaway |
| 6,213,972 B1 | 4/2001 | Butterfield et al. |
| 6,219,587 B1 | 4/2001 | Ahlin et al. |
| 6,221,011 B1 | 4/2001 | Bardy |
| 6,226,564 B1 | 5/2001 | Stuart |
| 6,230,927 B1 | 5/2001 | Schoonen et al. |
| 6,234,997 B1 | 5/2001 | Kamen et al. |
| 6,241,704 B1 | 6/2001 | Peterson et al. |
| 6,248,065 B1 | 6/2001 | Brown |
| 6,249,614 B1 | 6/2001 | Kolesnik et al. |
| 6,255,951 B1 | 7/2001 | De La Huerga |
| 6,256,967 B1 | 7/2001 | Hebron et al. |
| 6,259,355 B1 | 7/2001 | Chaco et al. |
| 6,259,654 B1 | 7/2001 | de la Huerga |
| 6,263,312 B1 | 7/2001 | Kolesnik et al. |
| 6,266,645 B1 | 7/2001 | Simpson |
| 6,267,559 B1 | 7/2001 | Mossman et al. |
| 6,270,252 B1 | 8/2001 | Siefert |
| 6,272,481 B1 | 8/2001 | Lawrence et al. |
| 6,272,505 B1 | 8/2001 | De La Huerga |
| 6,283,322 B1 | 9/2001 | Liff et al. |
| 6,290,206 B1 | 9/2001 | Doyle |
| 6,290,650 B1 | 9/2001 | Butterfield et al. |
| 6,308,171 B1 | 10/2001 | De La Huerga |
| 6,317,719 B1 | 11/2001 | Schrier et al. |
| 6,321,203 B1 | 11/2001 | Kameda |
| 6,332,090 B1 | 12/2001 | DeFrank et al. |
| RE37,531 E | 1/2002 | Chaco et al. |
| 6,338,007 B1 | 1/2002 | Broadfield et al. |
| 6,339,732 B1 | 1/2002 | Phoon et al. |
| 6,345,260 B1 | 2/2002 | Cummings, Jr. et al. |
| 6,345,268 B1 | 2/2002 | de la Huerga |
| 6,346,886 B1 | 2/2002 | De La Huerga |
| 6,347,329 B1 | 2/2002 | Evans |
| 6,347,553 B1 | 2/2002 | Morris et al. |
| 6,348,777 B1 | 2/2002 | Brown et al. |
| 6,352,200 B1 | 3/2002 | Schoonen et al. |
| 6,355,916 B1 | 3/2002 | Siefert |
| 6,358,225 B1 | 3/2002 | Butterfield |
| 6,363,282 B1 | 3/2002 | Nichols et al. |
| 6,364,834 B1 | 4/2002 | Reuss et al. |
| 6,370,841 B1 | 4/2002 | Chudy et al. |
| 6,381,577 B1 | 4/2002 | Brown |
| 6,405,165 B1 | 6/2002 | Blum et al. |
| 6,407,335 B1 | 6/2002 | Franklin-Lees et al. |
| 6,408,330 B1 | 6/2002 | DeLaHuerga |
| 6,434,567 B1 | 8/2002 | De La Huerga |
| 6,434,569 B1 | 8/2002 | Toshimitsu et al. |
| 6,449,927 B2 | 9/2002 | Hebron et al. |
| 6,464,667 B1 | 10/2002 | Kamen et al. |
| 6,475,146 B1 | 11/2002 | Frelburger et al. |
| 6,475,148 B1 | 11/2002 | Jackson et al. |
| 6,516,321 B1 | 2/2003 | De La Huerga |
| 6,519,569 B1 | 2/2003 | White et al. |
| 6,544,228 B1 | 4/2003 | Heitmeier |
| 2001/0001237 A1 | 5/2001 | Stroda et al. |
| 2001/0003177 A1 | 6/2001 | Schena et al. |
| 2001/0007932 A1 | 7/2001 | Kamen et al. |
| 2001/0017817 A1 | 8/2001 | De La Huerga |
| 2001/0028308 A1 | 10/2001 | De La Huerga |
| 2001/0032101 A1 | 10/2001 | Statius Muller |
| 2001/0037220 A1 | 11/2001 | Merry et al. |
| 2001/0044731 A1 * | 11/2001 | Coffman et al. |
| 2002/0002473 A1 | 1/2002 | Schrier et al. |
| 2002/0016719 A1 | 2/2002 | Nemeth et al. |
| 2002/0016722 A1 | 2/2002 | Kameda |
| 2002/0019748 A1 | 2/2002 | Brown |
| 2002/0029157 A1 | 3/2002 | Marchosky |
| 2002/0032602 A1 | 3/2002 | Lanzillo, Jr. et al. |
| 2002/0038392 A1 | 3/2002 | De La Huerga |
| 2002/0044043 A1 | 4/2002 | Chaco et al. |
| 2002/0046062 A1 | 4/2002 | Kameda |
| 2002/0046346 A1 | 4/2002 | Evans |
| 2002/0067273 A1 | 6/2002 | Jaques et al. |
| 2002/0077865 A1 | 6/2002 | Sullivan |
| 2002/0082480 A1 | 6/2002 | Riff et al. |
| 2002/0082865 A1 | 6/2002 | Bianco et al. |
| 2002/0082868 A1 | 6/2002 | Pories et al. |
| 2002/0084904 A1 | 7/2002 | De La Huerga |
| 2002/0107707 A1 | 8/2002 | Naparstek et al. |

| | | | |
|---|---|---|---|
| 2002/0116509 | A1 | 8/2002 | DeLaHuerga |
| 2002/0128880 | A1 | 9/2002 | Kunikiyo |
| 2002/0133377 | A1 | 9/2002 | Brown |
| 2002/0143254 | A1 | 10/2002 | Maruyama |
| 2002/0174105 | A1 | 11/2002 | De La Huerga |

FOREIGN PATENT DOCUMENTS

| | | |
|---|---|---|
| DE | 3922026 A1 | 1/1991 |
| DE | 9308204 | 9/1993 |
| DE | 4339154 A1 | 5/1995 |
| EP | 0233115 A1 | 8/1987 |
| EP | 0 300 552 A1 | 1/1989 |
| EP | 0384155 A2 | 8/1990 |
| EP | 0 505 627 A2 | 9/1992 |
| EP | 0 531 889 A2 | 3/1993 |
| EP | 0 595 474 A2 | 5/1994 |
| EP | 0633035 A1 | 1/1995 |
| EP | 0 652 528 A2 | 5/1995 |
| EP | 0 672 427 A1 | 9/1995 |
| FR | 2266641 | 10/1975 |
| FR | 2555744 A1 | 5/1985 |
| GB | 0 279 784 A | 1/1995 |
| GB | 0 285 135 A | 6/1995 |
| WO | WO 8400493 A2 | 2/1984 |
| WO | 89/08264 A1 | 9/1989 |
| WO | WO 91/00307 A1 | 1/1991 |
| WO | WO 91/04759 A1 | 4/1991 |
| WO | WO 91/05310 A1 | 4/1991 |
| WO | 0 462 466 A2 | 12/1991 |
| WO | WO 92/12402 A1 | 7/1992 |
| WO | WO 93/00047 A1 | 1/1993 |
| WO | WO 93/02720 A1 | 2/1993 |
| WO | WO 9321978 A1 | 11/1993 |
| WO | WO 94/05355 A1 | 3/1994 |
| WO | WO 94/08647 A1 | 4/1994 |
| WO | WO 94/12235 A1 | 6/1994 |
| WO | WO 94/24929 A1 | 11/1994 |
| WO | WO 95/02426 A1 | 1/1995 |
| WO | WO 95/20199 A1 | 7/1995 |
| WO | WO 95/20804 A1 | 8/1995 |
| WO | WO 95/24010 A1 | 9/1995 |
| WO | WO 95/26009 A1 | 9/1995 |
| WO | WO 95/32480 A1 | 11/1995 |
| WO | WO 96/16685 A1 | 6/1996 |
| WO | WO 99/10029 A1 | 3/1999 |
| WO | WO 99/44162 A1 | 9/1999 |
| WO | WO 00/43941 A1 | 7/2000 |
| WO | WO 00/72181 | 11/2000 |
| WO | WO 01/39816 A2 | 6/2001 |
| WO | WO 01/88828 A2 | 11/2001 |

OTHER PUBLICATIONS

Endo, A.S., "Using Computers In Newborn Intensive Care Settings," *American Journal of Nursing*, Jul. 1981, pp. 1336–1337.

Wareham, D.V., Johnson, S.R., Tyrrell, T.J., "Combination Medication Cart and Computer Terminal in Decentralized Drug Distribution," *American Journal of Hospital Pharmacy*, Jun. 1983, pp. 976–978, vol. 40.

Barker, K.N., Pearson, R.E., Hepler, C.D., Smith, W.E., Pappas, C.A., "Effect of an automated bedside dispensing machine on medication errors," *American Journal of Hospital Pharmacy*, Jul. 1984, pp. 1352–1358, vol. 41 No. 7.

Cook, A.A., "An integrated nursing–pharmacy approach to a computerized medication dispensing/administration system," *hospital pharmacy*, May 1985, pp. 321, 324–325, vol. 20.

Perlstein, P.H., "Future Directions for Device Design and Infant Management," *Medical Instrumentation*, Feb. 1987, pp. 36–41, vol. 21 No. 1.

Mackin, M.H., "Impact of Technology on Environmental Therapeutic Device Design," *Medical Instrumentation*, Feb. 1987, pp. 33–35, vol. 21 No. 1.

Pesce, J., "Bedside Terminals: MedTake," *M.D. Computing*, Jan./Feb. 1988, pp. 16–21, vol. 5 No. 1.

Hughes, S., "Bedside Terminals: Clinicom," *M.D. Computing*, Jan./Feb. 1988, pp. 22–28, vol. 5 No. 1.

Gammon, K., Robinson, K., "Bedside Data System Aids Pharmacy," *Computers in Healthcare*, Dec. 1988, pp. 35–37, vol. 9 No. 12.

Barry, G.A., Bass, Jr., G.E., Eddlemon, J.K., Lambert, L.L., "Bar–code technology for documenting administration of large–volume intravenous solutions," *American Journal of Hospital Pharmacy*, Feb. 1989, pp. 282–287, vol. 46.

Cote, D.D., Torchia, M.G., "Robotic system for i.v. antineoplastic drug preparation: Description and preliminary evaluation under simulated conditions," *American Journal of Hospital Pharmacy*, Nov. 1989, pp. 2286–2293, vol. 46.

Graseby 3100 Syringe Pump, Graseby Medical Ltd., A Cambridge Electronic Industries Company, England, 2 pages.

Lefkowitz, S., Cheiken, H., Barnhart, M.R., "A Trial of the Use of Bar Code Technology to Restructure a Drug Distribution and Administration System," *hospital pharmacy*, Mar. 1991, pp. 239–242, vol. 26.

Meyer, G.E., Brandell, R., Smith, J.E., Milewski, Jr., F.J., Brucker, Jr., P., Coniglio, M., "Use of bar codes in inpatient drug distribution," *American Journal of Hospital Pharmacy*, May 1991, pp. 953–966, vol. 48.

Kampmann, J., Lau, G., Kropp, St. Schwarzer, E., Hernandez Sande, C., "Connection of electronic medical devices in ICU according to the standard 'MIB'," *International Journal of Clinical Monitoring and Computing*, 1991, pp. 163–166, vol. 8.

Dito, W.R., McIntire, S., Leano, J., "Bar codes and the clinical laboratory: adaptation perspectives," *Clinical Laboratory Management Review*, Jan./Feb. 1992, pp. 72–85.

Abdoo, Y.M., "Designing a Patient Care Medication and Recording System That Uses Bar Code Technology," *Computers in Nursing*, May/Jun. 1992, pp. 116–120, vol. 10 No. 3.

50 Ways to Touch Memory, Second Edition, Dallas Semiconductor, Dallas, Texas, Oct. 1992, pp. 1–26.

Atherton, H.D., Dollberg, S., Donnelly, M.M., Perlstein, P.H., Hoath, S.B., "Computerized Temperature Control of the Low–Birth–Weight Infant: A 20–Year Retrospective and Future Prospects," *Biomedical Instrumentation and Technology*, Jul./Aug. 1994, pp. 302–309, vol. 28 No. 4.

Perini, V.J., Vermeulen, Jr., L.C., "Comparison of automated medication–management systems," *American Journal of Hospital Pharmacy*, Aug. 1, 1994, pp. 1883–1891, vol. 51.

Friesdorf, W., Groβ–Alltag, F., Konichezky, S., Schwilk, B., Fattroth, A., Fett, P., "Lessons learned while building an integrated ICU workstation," *International Journal of Clinical Monitoring and Computing*, 1994, pp. 89–97, vol. 11.

Puckett, F., "Medication–management component of a point–of–care information system," *American Journal of Health–System Pharmacists*, Jun. 15, 1995, pp. 1305–1309, vol. 52.

International Search Report, mailed Apr. 14, 2004 from the European Patent Office, in connection with International Application No. PCT/US02/38904, filed May 12, 2002 by Applicant Baxter International Inc.

* cited by examiner

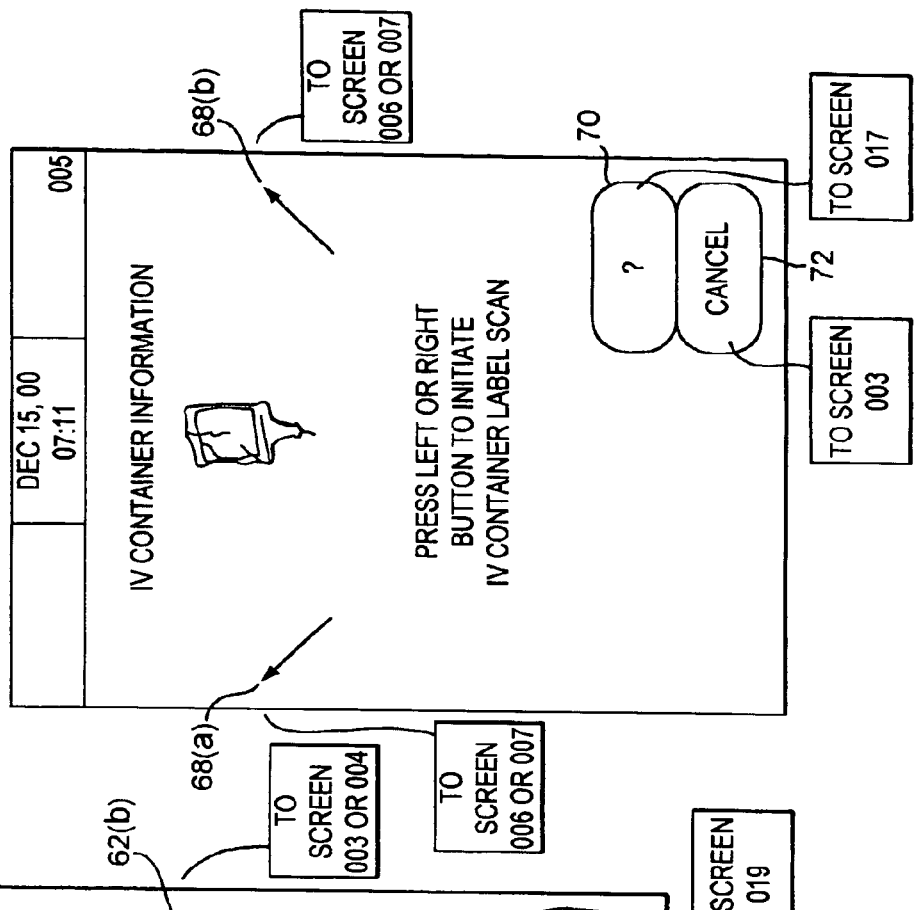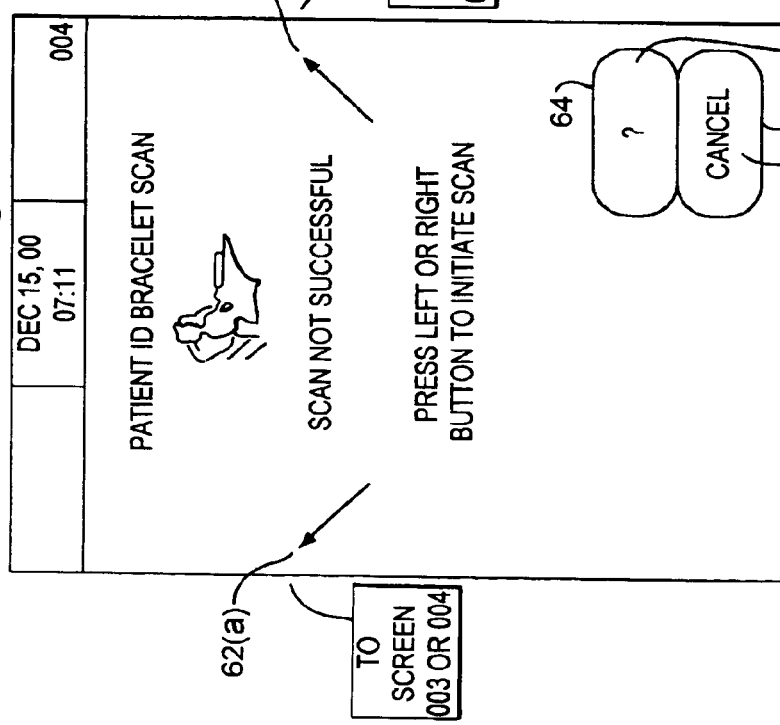

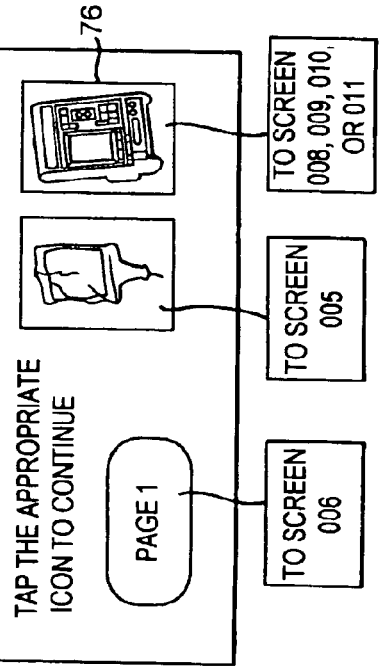

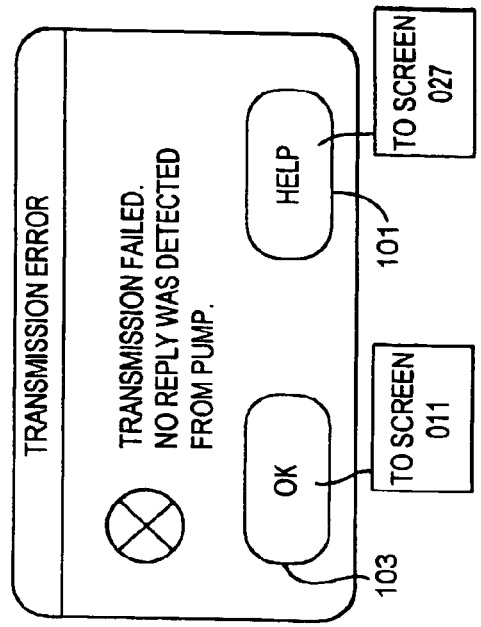
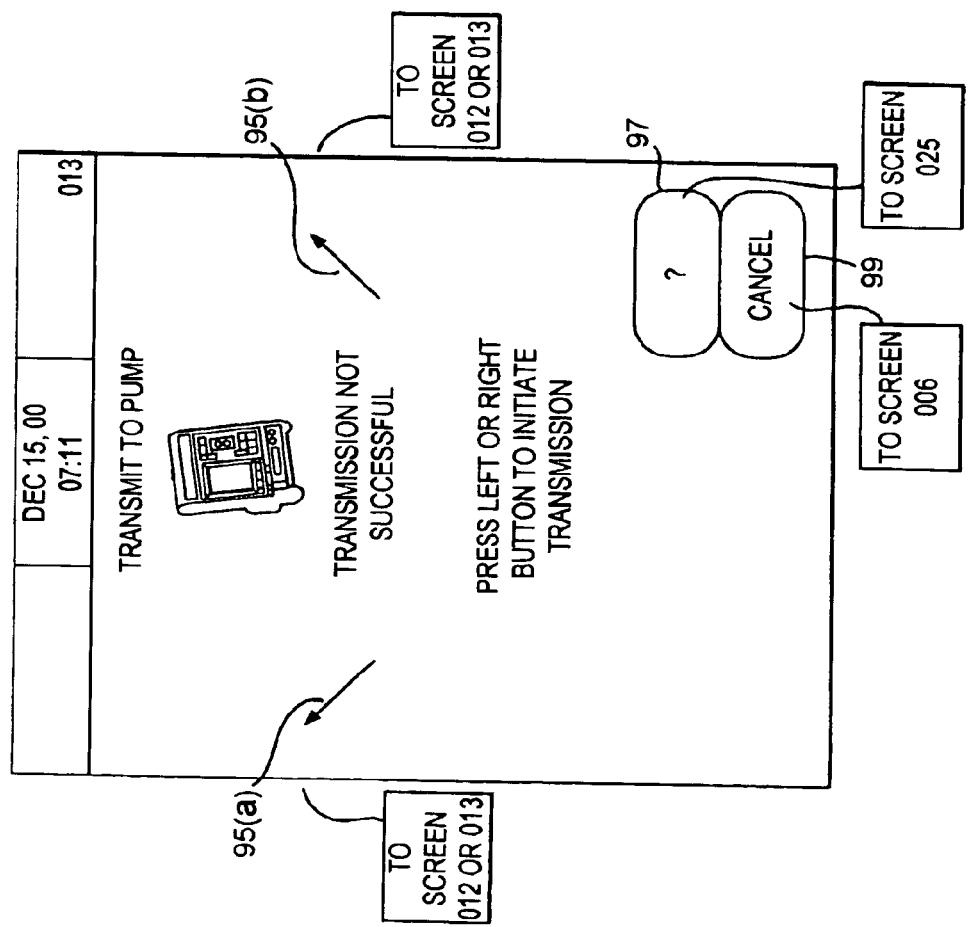

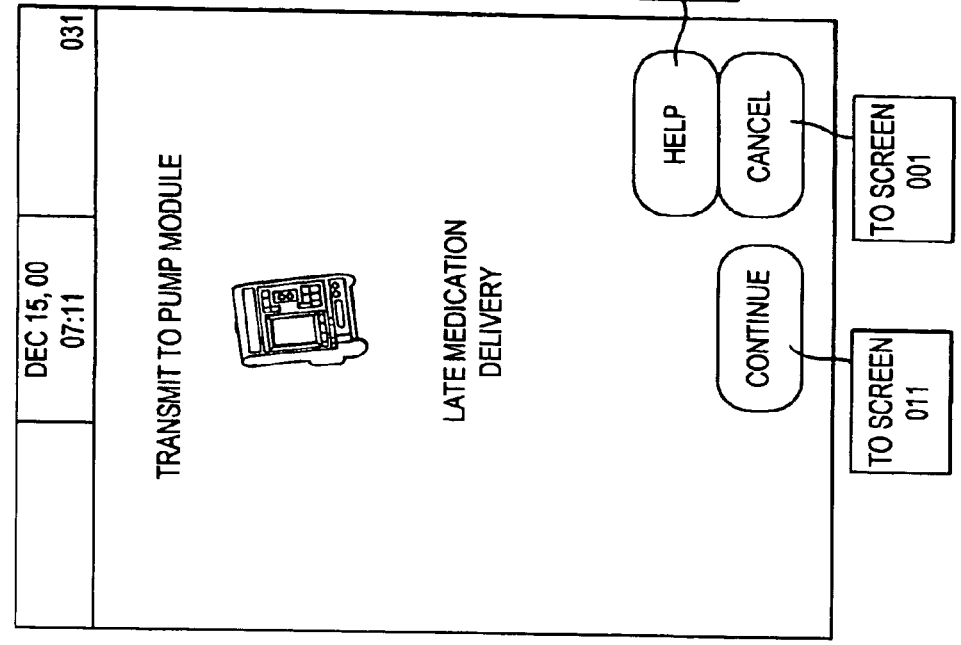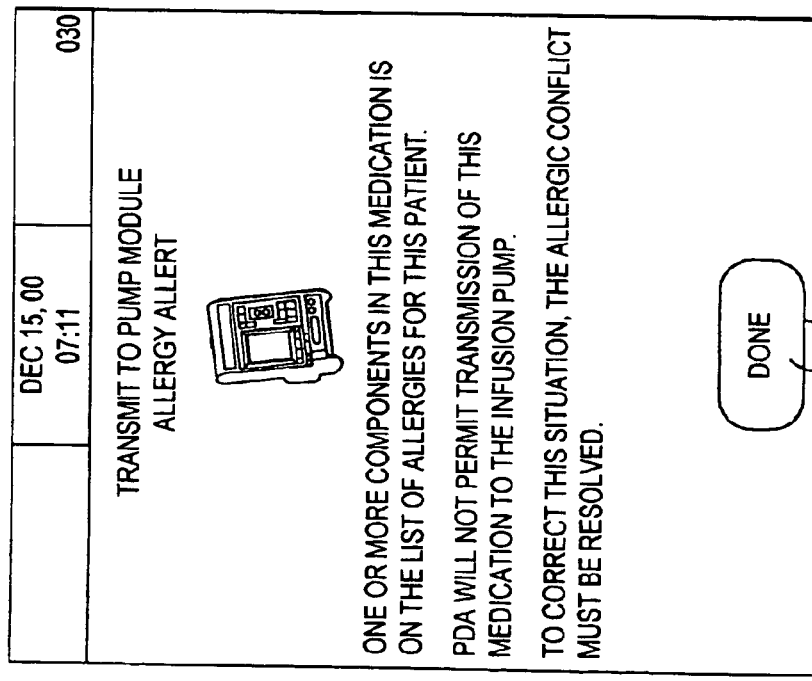

FIG. 16

```
| DEC 15, 00          014 |
| 07:11                   |

PATIENT ID: B0031900318

PATIENT NAME: HITCHCOCK, JAMES R  WEIGHT: 75Kg

PATIENT LOCATION: ROOM 211  BED 2

MEDICAL RECORD #: 863291

DATE OF BIRTH:      07/11/79       AGE:  21 YEARS

DATE OF ADMISSION: 11/15/00        SEX:  M

PRIMARY PHYSICIAN: DR. BUI ( CONTINUE )
```

CONTINUE → TO LAST ACTIVE SCREEN

FIG. 17

```
| DEC 15, 00          015 |
| 07:11                   |

PATIENT INFORMATION
               HELP

TO SCAN THE PATIENT'S ID BRACELET:

1. AIM THE BAR CODE SCANNER HEAD AT THE BAR
   CODE LOCATED ON THE PATIENT ID BRACELET.

2. POSITION THE BAR CODE SCANNER WINDOW
   FROM ONE TO FIVE INCHES FROM THE BAR CODE.

3. PRESS THE LEFT OR RIGHT BUTTON TO INITIATE
   THE PATIENT ID BRACELET SCAN.

( CANCEL )
```

CANCEL → TO SCREEN 002

FIG. 18

| DEC 15, 00 | | 016 |
|---|---|---|
| | 07:11 | |

PATIENT ID: B0031900318
PATIENT NAME: HITCHCOCK, JAMES R    WEIGHT: 75 Kg
PATIENT LOCATION: ROOM 211  BED 2

ORDER #: 3265894            BAG ID: 001215-01
MEDICATION: D5W WITH 20 mEg KCI
VOLUME: 1000 mL    RATE: 125 mL/hr

PREPARED BY: J. FROBEL    12/14/00  4:29 PM
SOLUTION EXPIRES AT  7:00 PM ON 12/15/00
DELIVERY TIME TO PATIENT: 12/15/00 AT 07:00
ADMINISTRATION ROUTE: PERIPHERAL

HUNG BY: J. SMITH           AT: 12/15/00 07:11

[ CONTINUE ] → TO LAST ACTIVE SCREEN

FIG. 19

| DEC 15, 00 | | 017 |
|---|---|---|
| | 07:11 | |

IV CONTAINER INFORMATION
HELP

TO SCAN THE IV CONTAINER BAR CODE:

1. AIM THE BAR CODE SCANNER HEAD AT THE BAR CODE LOCATED ON THE IV CONTAINER LABEL
2. POSITION THE BAR CODE SCANNER WINDOW FROM ONE TO FIVE INCHES FROM THE BAR CODE
3. PRESS THE LEFT OR RIGHT BUTTON TO INITIATE THE IV CONTAINER LABEL SCAN

[ CANCEL ] → TO SCREEN 005

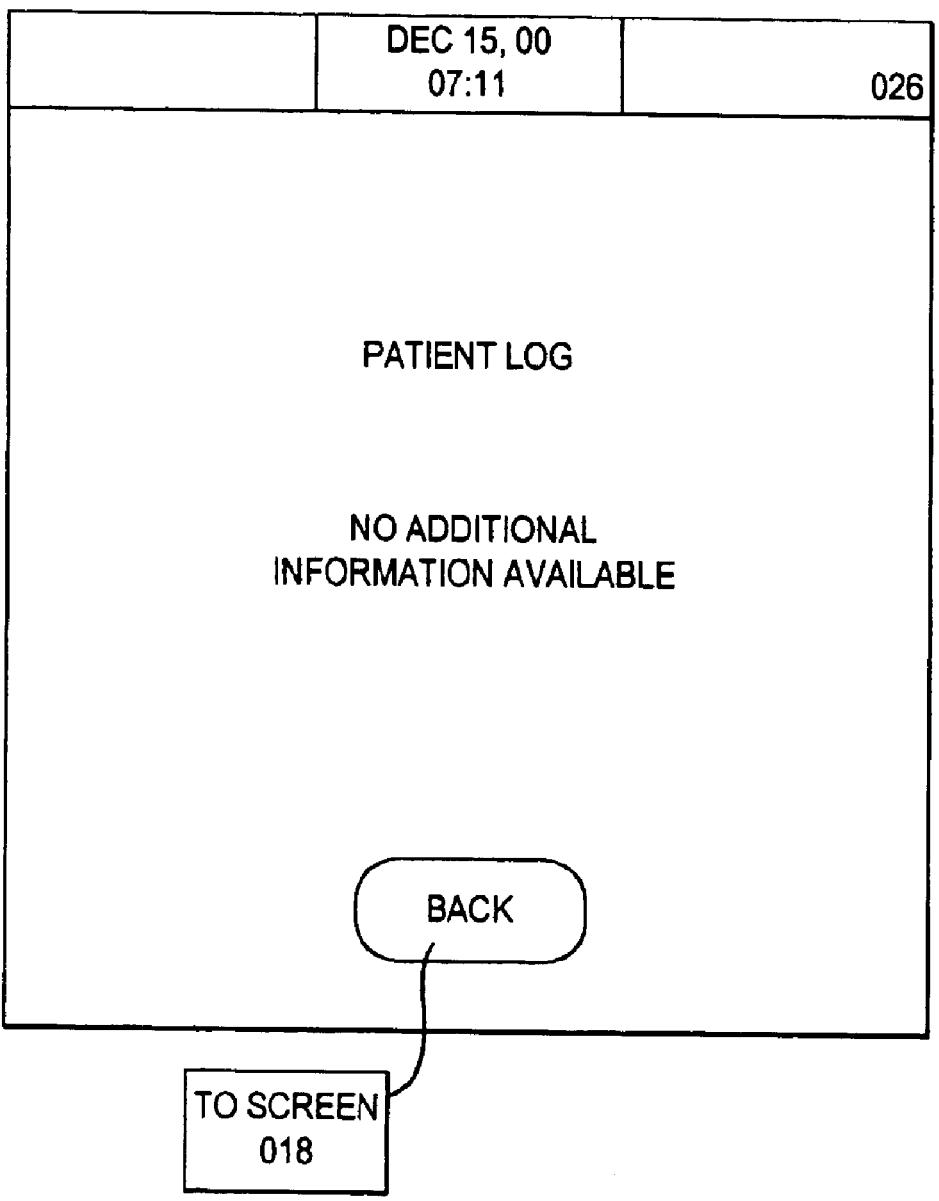

FIG. 29(a)

```
                                          035
┌─────────────────────────────────────────────┐
│  DEC 15, 00                                 │
│  07:11                                      │
├─────────────────────────────────────────────┤
│              IV CONTAINER SCAN              │
│                                             │
│  PATIENT ID: B0031900318    WEIGHT: 75 Kg   │
│  NAME: HITCHCOCK, JAMES R                   │
│  LOCATION: ROOM 211  BED 2                  │
│                                             │
│  ORDER #: 3265894       BAG ID: 001215-01   │
│  SEC MEDICATION: ZYTHROMAX                  │
│  VOLUME: 50 mL   RATE:   50 mL/hr           │
│  DELIVERY TO PATIENT: 12/15/00  AT 7:00     │
│                                             │
│                                             │
│  TAP THE APPROPRIATE                        │
│  ICON TO CONTINUE                           │
│                                             │
│     ( PAGE 2 )      [bag]        [device]   │
└─────────────────────────────────────────────┘
      │                  │              │
  TO SCREEN          TO SCREEN      TO SCREEN
    036                 005         008, 009, 010
                                       or 011
```

FIG. 29(b)

```
                                          036
┌─────────────────────────────────────────────┐
│  DEC 15, 00                                 │
│  07:11                                      │
├─────────────────────────────────────────────┤
│              IV CONTAINER SCAN              │
│                                             │
│  PATIENT ID: B0031900318    WEIGHT: 75 Kg   │
│  NAME: HITCHCOCK, JAMES R                   │
│  LOCATION: ROOM 211  BED 2                  │
│                                             │
│  PREPARED BY:  J. FROBEL                    │
│  SOLUTION EXPIRES: 7:00 PM ON 12/15/00      │
│  TO BE DELIVERED WITH:   BAG ID 001215-01   │
│  ADMINISTRATION ROUTE: PERIPHERAL           │
│                                             │
│  TAP THE APPROPRIATE                        │
│  ICON TO CONTINUE                           │
│                                             │
│     ( PAGE 1 )      [bag]        [device]   │
└─────────────────────────────────────────────┘
      │                  │              │
  TO SCREEN          TO SCREEN      TO SCREEN
    035                 005         008, 009, 010
                                       or 011
```

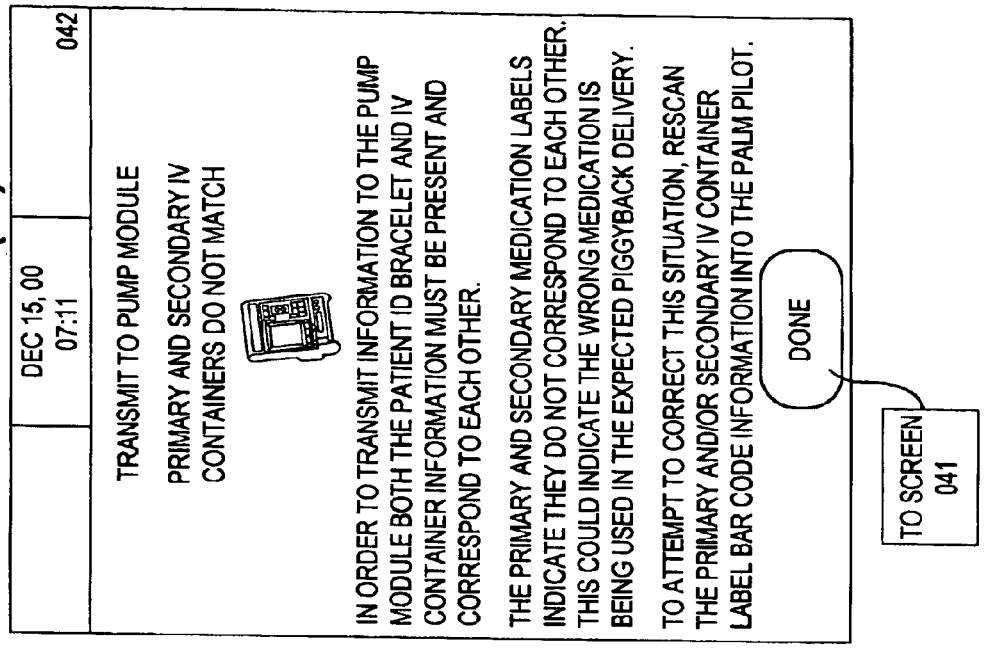
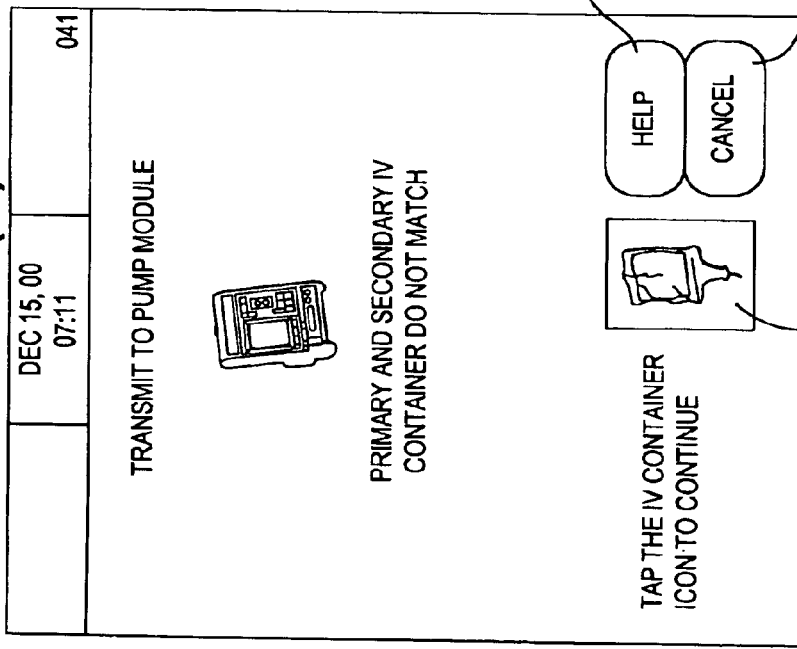

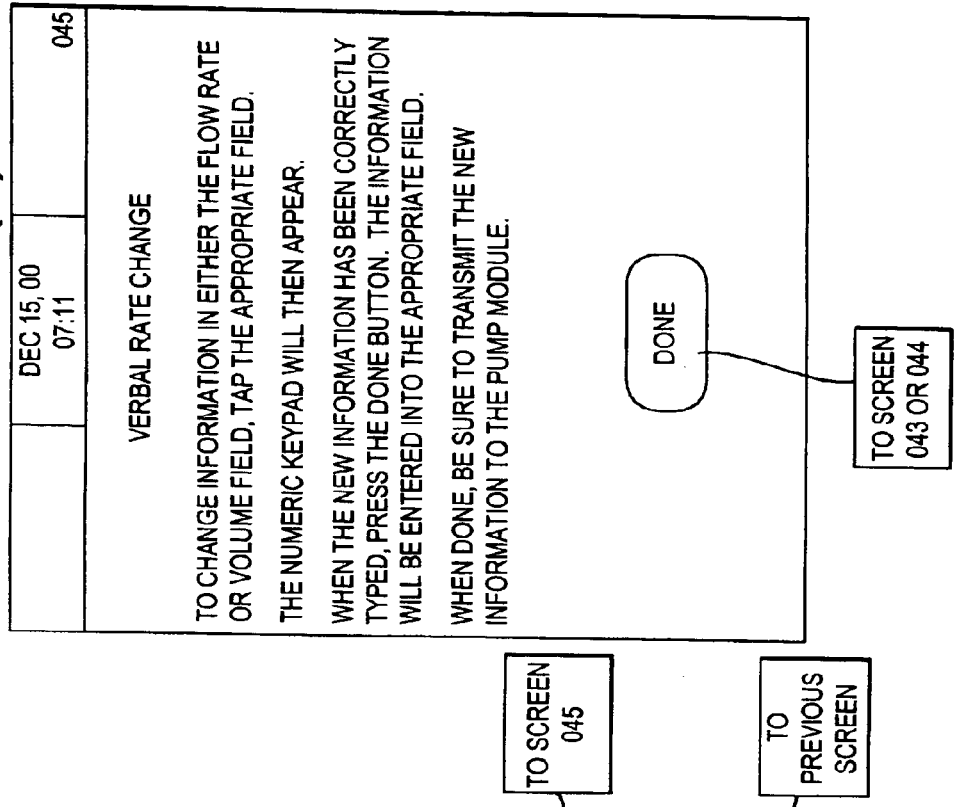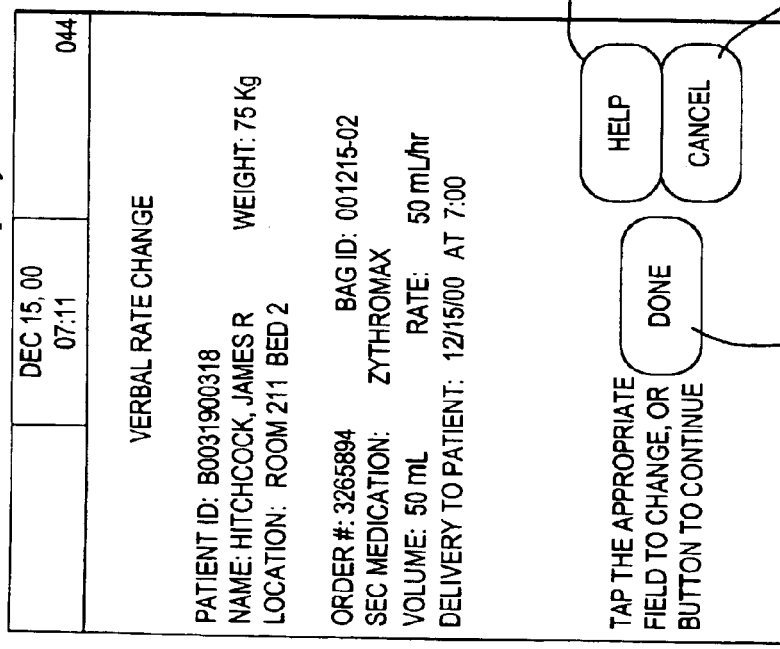

END RESULT: SYSTEM OPERATES

FIG. 38

MULTIPLE CONTAINERS

SELECT THE PRIMARY AND SECONDARY MEDICATIONS....

MEDICATION: [____]
◉ PRIMARY   ○ SECONDARY

MEDICATION: [____]
○ PRIMARY   ◉ SECONDARY

[CANCEL]   [OK]

FIG. 37

MULTIPLE CONTAINERS

SELECT THE MEDICATION YOU WANT TO USE....

MEDICATION: [____]
☑ KEEP THIS MEDICATION

MEDICATION: [____]
☑ KEEP THIS MEDICATION

MEDICATION: [____]
☑ KEEP THIS MEDICATION

[CANCEL]   [OK]

MEDICATION DELIVERY SYSTEM

TECHNICAL FIELD

The present invention is directed to a medication delivery system and in particular, a medication delivery system that reduces potential medication errors by delivering the right dose to the right patient with the right drug at the right time and by the right route.

BACKGROUND OF THE INVENTION

According to a 1999 Institute of Medicine Report, human error contributes to approximately 70,000–100,000 deaths per year caused by "medical errors." As a designation, medical errors are associated with a multitude of circumstances and causes. However, studies show that a significant percentage of serious errors are associated with the administration of intravenous (IV) medication.

A patient's response to drugs delivered intravenously is rapid because the gastrointestinal system is bypassed. Thus, if an error is made, there is little time to compensate. Most critical drugs are delivered intravenously. Correct administration is a process that often involves several individuals for delivering an accurate dose of a drug to a particular patient at a prescribed time and through a particular administration route. It is not difficult to comprehend the potential for error, as well as the undesirable probability that the occurrence of an error can result in one or more detrimental effects to the patient.

An intravenous error may be induced at any time throughout the process of ordering, transcribing, dispensing, and administering a drug. For example, an ordering error may occur because an order is illegible, incomplete, or entered on the wrong patient's chart, because a decimal is misplaced or inappropriate, or unacceptable prescription abbreviations are used, or because an inappropriate drug is selected or a patient's allergies are not properly identified. Transcription errors may occur because an order was not transcribed, not completely signed off, or incorrectly transcribed onto the Medication Administration Record (MAR). Also, on occasion a patient's allergies are not transcribed or a transcription is illegible. Dispensing errors may occur with respect to the dose, or the identification of the medication or patient. An administration error may occur at any time during the course of a patient's care and may concern the patient or drug identification, or the time, dose, or route of drug administration. It is notable that research indicates that 60–80% of intravenous errors are attributed to humans. It follows then that one way to reduce the potential for error is to automate as much as possible the process of drug ordering, transcribing, dispensing, and administering.

Information technology may be utilized for automating portions of the drug ordering, transcribing, dispensing, and administration process. For example, the potential for error may be reduced by cross referencing infusion data used to program a pump and also by reviewing data programmed into a pump prior to enabling the pump to operate and also by detecting if programmed data is changed.

One system for collecting data and managing patient care is disclosed in U.S. Pat. No. 5,781,442 issued to Engleson et al. The system may include a pharmacy computer, a nursing station computer, and bedside computers that may be connected to clinical devices such as infusion pumps. The various computers are connected together via a local area network. The computers have memory for storing certain information relating to a patient's care and information can be inputted into the computers. The pharmacy computer will compare information communicated from the bedside computer to information stored in the pharmacy computer. If the comparison satisfies a predetermined condition, the pharmacy computer downloads clinical device operating parameters to the bedside computer. The bedside computer, in turn, programs the clinical device to operate in accordance with the downloaded operating parameters. The comparison of data is only performed by the pharmacy computer. This system requires several computers as a computer is required at each bedside in order to program the clinical device.

Another system for automatically entering into an infusion pump patient identification and drug data is disclosed in U.S. Pat. No. 5,317,506 (Coutre et al.), entitled "Infusion Fluid Management System." The '506 patent is directed at a pharmacy management system and an infusion pumping system in combination for managing and analyzing prescribed infusion programs. In this system, patient and IV container information is provided in machine readable format. This information is read by a bar code reader attached to the pump. The pump has a processor that is programmed to compare the patient information to the IV container information. This system requires, therefore, that each pump be programmed (or reprogrammed) to compare the patient data to medication data. Also, if an allergy check is desired, the pump must also be programmed with a patient's allergies. Other encumbrances to such a system stem from the requirement that the pump must be able to read the patient code and the IV container code. Because pumps are mobilized frequently, disconnecting them from power and wired data communication, as well as programming the pumps with prescription data and verifying the prescription data in a mobile environment is important. The physical location of the patient code (which is usually attached to the patient) and IV container code in relation to the pump is an important, and potentially limiting, consideration. Also, changes made to data formats, such as from 1-dimensional bar code to 2-dimensional bar code, must be reprogrammed into each pump, as well as patient allergies and any other data that is or may be desirable for administering patient therapy. Further, the system of the '506 patent does not provide for an ancillary check on the pump programming data and operational instructions. Information is input into the pump without any prior check for accuracy or completeness and there is no separate system in place for reviewing programmed and operational information to ensure that it is not inaccurate, imprecise, and/or improper.

Accordingly, a need remains for a system that provides a check on patient and pump data prior to pump programming, automatically transmits checked infusion data to the pump, is easily configurable, reconfigurable, and mobile in application, and can verify and check that data programmed into the pump and pump operational data remain correct and unchanged.

The present invention is provided to solve these and other problems.

SUMMARY OF THE INVENTION

The present invention is directed to a medication delivery system, in particular, a medication delivery system that reduces potential medication errors by delivering the right dose to the right patient with the right drug at the right time and by the right route. The system can also be configured for solely monitoring.

A medication delivery system having features of the present invention comprises a medical container holding a prescribed medication to be delivered to a patient, a tag adapted to be worn by the patient, a handheld computing device, and an electronic medication delivery device. Data on the medication is contained in a first label on the medication container. The first label also contains the instruction on how the medication is delivered to the patient, including the appropriate settings for an electronic medication delivery device for delivering the medication to the patient. Patient data is contained in a second label on the tag worn by the patient. The medication data, medication delivery instruction, and patient data are provided in machine readable formats. The handheld computing device reads the medication data and the medication delivery instruction on the medication container and the patient data on the patient tag. The handheld computing device stores the information obtained and performs a matching check to confirm that the medication data matches with the patient data. Upon a confirmed match, it transmits the medication delivery instruction to the electronic medication delivery device, which downloads the instruction, programs the delivery device, and prompts an operator to begin delivering the medication to the patient according to the downloaded instruction. In an alternative form of the invention, the medication delivery device can be a general medical device such as a device for monitoring data.

In a preferred embodiment of the present invention, the medication container is an IV bag, the prescribed medication is an IV drug, the patient tag is a bracelet worn by the patient, the handheld computing device is a personal digital assistant (PDA), and the electronic medication delivery device is a programmable infusion pump. The medication data, medication delivery instruction, and the patient data are provided as two-dimensional bar codes to be read by a bar code scanner incorporated into the personal digital assistant. The communication between the personal digital assistant to the electronic infusion pump is via infrared transmission. The programmable pump may further comprise an adapter which facilitates the communication between the PDA and the infusion pump, and reviews data programmed into the pump and pump operational parameters.

The system of the present invention may also be configured to deliver multiple medications.

The present invention is also directed to a method of medication delivery to reduce medication errors according to the features disclosed in the invention.

Other features and advantages of the invention will become apparent from the following description taken in conjunction with the following drawings.

BRIEF DESCRIPTION OF THE DRAWINGS

FIGS. 2–34 are examples of displays provided on a computing device in accord with one embodiment of the present invention;

FIGS. 37–39 are additional examples of displays provided on a computing device in accord with one embodiment of the present invention.

DETAILED DESCRIPTION

Figure 1:
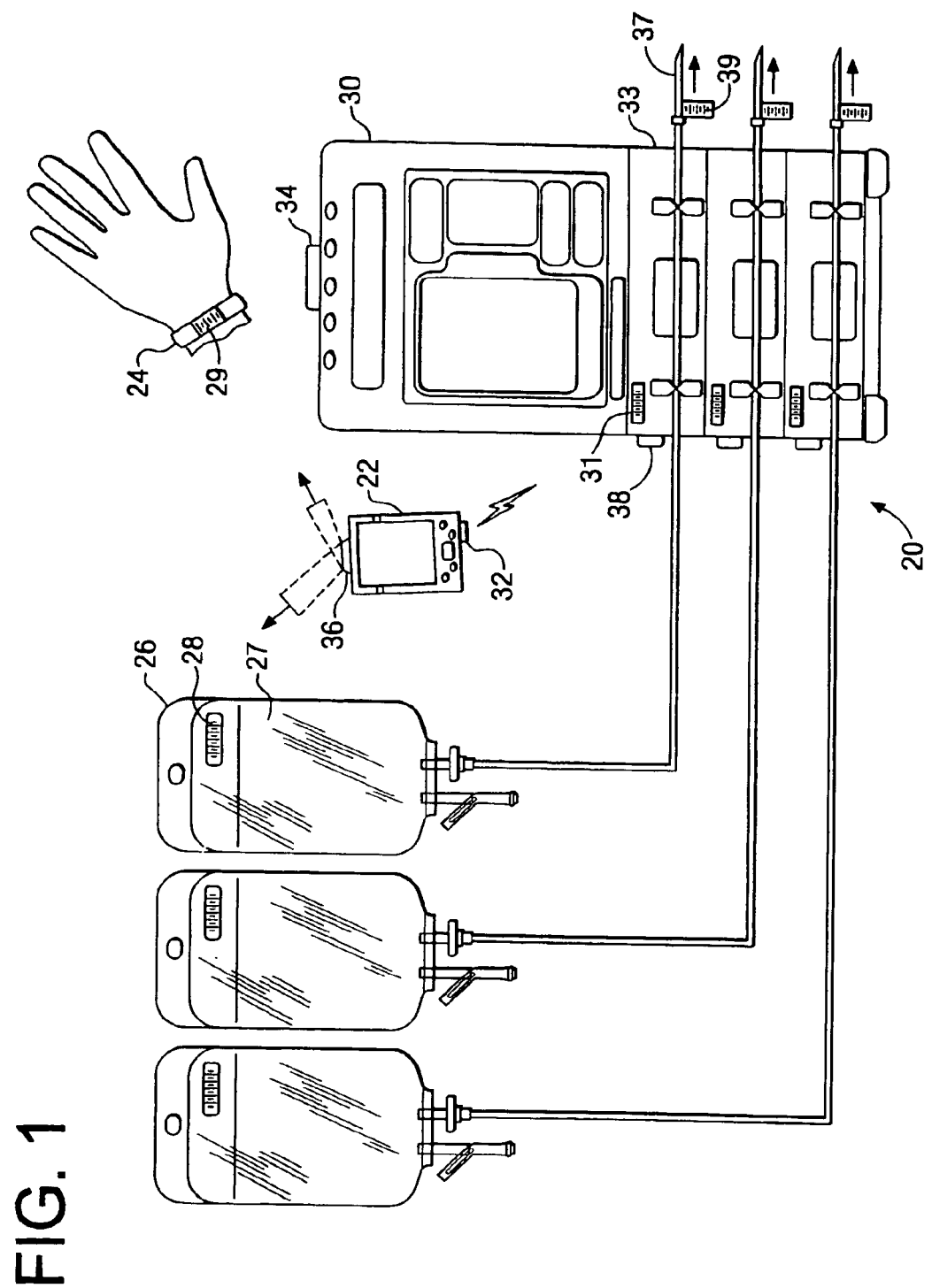
FIG. 1 is a schematic view disclosing functional relationships between components of one embodiment of the present invention.

While this invention is susceptible of embodiments in many different forms, there is shown in the drawings and will herein be described in detail a preferred embodiment of the invention with the understanding that the present disclosure is to be considered as an exemplification of the principles of the invention and is not intended to limit the broad aspect of the invention to the embodiments illustrated.

Referring to the drawings, FIG. 1 shows a schematic view disclosing functional relationships between components of one embodiment of the present invention. A medication delivery system is generally disclosed and referred to with the reference numeral 20. The medication delivery system 20 generally comprises a medication container 26, a tag 24 adapted to be worn by a patient, a handheld computing device 22, and a medical device 30, which in one preferred embodiment, is a medication delivery device 30. The medication delivery system 20 can be configured to deliver medication in several different arrangements including parenteral and intravenous (e.g., non-oral) delivery.

The medication container 26 holds a prescribed medication 27. Information regarding the medication, which includes data on the medication and the specific instruction of delivering the medication to the patient is contained in a first label 28 on the medication container 26. The information is provided in machine readable format. Patient data is contained in a second label 29 on the tag 24 which is worn by the patient. This is typically in the form of a patient identification bracelet.

The handheld computing device 22 reads the medication data, medication delivery instruction, and patient data through a first information input device 36 integrated into the handheld computing device 22. The handheld computing device 22 stores the information and performs a matching check to confirm that the medication data match with the patient data, and that the medication is intended for the patient as prescribed. If the matching is confirmed, the handheld computing device 22 prompts the operator to manually confirm the match and to transmit and download the medication delivery instruction, via a first communication device 32, to the electronic medication delivery device 30, which receives the information by a second communication device 38 integrated with or connected to the medication delivery device 30. The medication delivery device 30 then prompts the operator to start delivering the medication 27 according to the instruction downloaded from the handheld computing device 22. The medication 27 is delivered to the patient via a catheter 37. The catheter 37 contains a label 39 to uniquely identify the catheter 37. The label 39 of the catheter 37, preferably a bar code label, also contains information regarding the catheter such as the type of catheter (e.g. central venous catheter, peripheral catheter, or epidural catheter).

The prescribed medication 27 in the present invention is typically a fluid, which includes both liquid formulations and gases. A preferred liquid formulation is an intravenous parenteral formulation. Examples of other parenteral liquid formulations suitable in the present invention are intrathecal, epidural, intra-arterial and the like. Examples of gas medications include the inhaled anesthetic gases such as sevoflurane, halothane, and enflurane. More than one medication may be delivered at the same time with the system 20. If more than one medication is being delivered, the medications may be held in the same container or separate containers. In intravenous infusions, it is common that additional medication(s) may be delivered as a piggyback. When multiple containers are used, each container is connected to a separate pump channel 33 on the delivery pump 30. Each pump channel 33 contains a label 31 with information to uniquely identify the channel. The label 31 for the pump channel 33 is preferably a bar code label. The handheld device will communicate the information read from the channel label 31 to the pump 30 so that the appropriate channel is activated. Alternatively, each pump channel 33 also has its own second communication device 38 to receive information from the handheld computing device 22. Any information to be downloaded to a particular pump channel 33 from the handheld device 22 has to match with the unique pump channel identification so that only the appropriate information is downloaded to the correct pump channel 33.

The medication container 26 in the present invention depends on the prescribed medication 27. Each medication has its own requirements on the specific container in which it is packaged. Examples of the container 26 include but are not limited to flexible plastic IV bags, plastic bottles, glass bottles, plastic syringes, glass syringes, and glass vials, and elastomeric devices.

Information regarding the prescribed medication 27 is contained in the first label 28 on the medication container 26. The first label 28 is preferably generated by the pharmacist preparing the medication who also attaches the first label 28 onto the medication container 26. Alternatively, the first label 28 can be generated by a drug manufacturer, such as the National Data Corporation (NDC) in the form of a NDC label. The information includes data on the medication 27 and instruction on how the medication 27 is to be delivered by the medication delivery device 30. The medication data may include but is not limited to: patient name, patient identification number, physician name, order number, date, drug name, drug amount, diluent amount, and route of administration. The delivery instruction which is to be transmitted and downloaded to the medication delivery device 30 may include but is not limited to: delivery rate, delivery volume, dose, dose time, duration of delivery, and duration of therapy. For an IV infusion pump, the medication delivery instruction may further include: primary rate, primary volume-to-be-infused (VTBI), piggyback VTBI, piggyback rate or time, primary dose mode, and pump channel identification. Optional text information may also be included in the first label 28, such as: patient name, patient identification number, physician name, drug name, diluent name, cautions, expiry, delivery time, location, prepared date, prepared time, and preparer identification. The pharmacy that generates the first label preferably includes a pharmacy information system (not shown) having a printer port. In one embodiment, the printer is connected directly to the printer port. In this configuration, the pharmacy information system may also be set-up to generate a print stream that will print a text label that may contain the medication data and delivery instruction. In one embodiment, the bar code label may be generated with the data derived from the generated print stream wherein the data is encoded onto the bar code label. This can be accomplished using a separate software application. In an alternate embodiment, the pharmacy information is configured to also communicate the actual medication information to the handheld computing device 22.

Patient data is contained in the second label 29 on the patient tag 24 adapted to be worn by the patient. The patient tag 24 is worn by the patient before the administration of the medication 27. In a preferred embodiment, the tag 24 is a bracelet to be worn by the patient on the wrist. The second label 29 is preferably generated by a hospital administrator based upon information in the hospital administration database. Patient data may include but is not limited to: patient name, patient identification number, and allergies. Optional text information may also be included in the second label 29, such as: patient name, patient identification number, medical record number, patient type, date of birth, age, sex, date of admit, and allergies.

In one embodiment, the second label 29 contains only the patient identification number. Other detailed patient information is stored in the handheld computing device 22. When the patient identification number is downloaded from the second label 29 into the handheld computing device 22, the detailed patient information is displayed on the handheld computing device 22.

As discussed, non-text medication information and patient data in the present invention is provided in machine readable formats. Examples of machine readable formats are: linear bar codes, two-dimensional bar codes such as the two-dimensional data matrix bar codes, other two-dimensional bar code symbologies, other printed data encoding techniques, smart tag or Radio Frequency Identification (RFID) technology, magnetic stripe or tape, Optical Character Recognition (OCR), optical hologram, and the like. The preferred format is the two-dimensional (2D) bar code, such as a 2D data matrix bar code, which provides a large amount of data in a condensed space with a very high readability. The 2D bar code is preferably generated by a software interface application that utilizes the print data stream from a pharmacy information system (PIS) and incorporates the appropriate data fields into the 2D bar code. A key benefit is the ability to generate bar code labels integrated with text without the support of the pharmacy system vendor. For economic and convenience reasons, it is preferred that the same format be used with both the first label 28 and second label 29 so that the information can be read by the same first information input device 36 on the handheld computing device 22. It is quite possible, however, to combine different machine readable formats in this design. For example, a first label 28 on the container 26 can be an RFID label and the second label 29 on the patient tag 24 can be a bar code label.

The handheld computing device 22 is equipped with: means for reading the prescribed medication data, the medication delivery instruction, and the patient data; means for storing information, and means to communicate with other electronic devices. It reads the medication data, medication delivery instruction, and patient data through the first information input device 36 integrated into the handheld computing device 22. It stores the information and performs a matching check to confirm that the medication data match with the patient data, and that the medication is intended for the patient as prescribed. The handheld computing device 22 may also display all or selected information stored. Suitable handheld computing devices include but are not limited to laptop or palmtop computers and personal digital assistants (PDA's). The preferred handheld computing device is a PDA such as a Palm™ Handheld, various handheld devices from Handspring™, and Pocket PC models from Compaq and Hewlett-Packard. Other brands are also possible. One major advantage of using a PDA is that it can be easily and inexpensively configured to meet the needs of the present invention. An added advantage is that the PDA may be used to provide additional software applications for use by the operator.

The first information input device 36 is integrated into the handheld computing device 22. The device 36 will correspond to the machine readable format selected for the medication information and patient data. Such device includes bar code readers, smart tag readers, magnetic stripe or tape readers, and optical readers. In a preferred embodiment in which the two-dimensional bar codes are employed, the appropriate information input device is a two-dimensional data matrix bar code scanner, such as Symbol's model 2740 bar code scanner. This bar code scanner is equipped with a charge coupled device (CCD) imager which can capture signatures or other photographic evidence electronically. An example of a CCD imager is a complimentary metal oxide semiconductor (CMOS) device. Once the medication information and patient data are captured by the handheld computing device 22 via the first information input device 36, the information is stored in the handheld computing device 22. The means for storing data within the handheld device 22 includes, for example, various types of memories, cache, magnetic storage, compact disc, optical storage, and the like. A software application is utilized to guide the nurse clinician through the process of checking the prescription against the patient and the handheld computing device 22 displays whether the data is incompatible, unreadable, incomplete, or amiss for some other reason. If the data is complete and compatible, the handheld computing device 22 is programmed to prompt the operator to transmit and download the medication delivery instruction to the medication delivery device 30. The transmission and downloading is via the first communication device 32 integrated into the handheld computing device 22 for reception by the second communication device 38 integrated into or connected to the medication delivery device 30. The preferred technology for such transmission is infrared transmission in which the first communication device 32 is an infrared transceiver and the pump adapter 34 and second communication device 38 are infrared transceivers in communication with the medication delivery device 30. Alternate methods of communication include wireless communication such as IEEE 802.11, Bluetooth® communication, radio frequency communication, optical communication or wired communication.

The medical device 30 can be a number of different devices. For example, the medical device 30 can be a monitoring device programmed with alarm limits etc. In a preferred embodiment, the medication device 30 is a medication delivery device 30. The medication delivery device 30 also depends on the prescribed medication 27 being administered to the patient. For example, electronic IV infusion pumps or syringe pumps are suitable for intravenous parenteral drugs while inhaled gases can be administered via a ventilator or respirator. The delivery device 30 includes a main processor for controlling operation, including a display and user interface. It is programmable automatically and remotely through a remote input device, such as the handheld computing device 22 of this invention.

In one embodiment in which the delivery device 30 has limited programming and communicating capabilities, the delivery device 30 further comprises a programmable adapter 34 for facilitating the communication, preferably via an infrared transceiver, between the handheld computing device 22 and the medication delivery device 30. The adapter 34 is programmed for reviewing delivery device programming data. The adapter 34 includes hardware and a processor programmed for receiving the prescription data from the handheld computing device 22, determining whether the received prescription data is consistent with operational data input directly to the medication delivery device 30, and enabling the delivery device 30 for operation. In this embodiment, the adapter processor is programmed to guard against incorrect initial programming of the delivery device 30 or incorrect changes in delivery device settings by monitoring the operation of the delivery device 30 and determining whether there is a rate, dose, or drug mismatch or whether the drug is of an incorrect concentration. If the adapter 34 detects an incorrect parameter at the delivery device 30, either at the start or during the operation of the delivery device, it sends an alarm signal to alert the operator of the incorrect parameter. In one embodiment, the alarm signal is sent to the handheld computing device 22. The adaptor 34 may be further programmed to transmit delivery device configuration data and manually programmed delivery device operation data to and receive delivery rate information from the handheld computing device 22. It is understood that a delivery device may have integrated programming and communicating capabilities wherein the adapter 34 is unnecessary.

In one embodiment, the delivery device 30 determines either a STOP or RUN delivery status signal based upon the operational data of delivery device 30. If the status signal is RUN (i.e., the data matches), the delivery device 30 periodically compares delivery device operational data, including delivery rate data, with the medication delivery instruction contained in the first label 28 on the medical container 26 during the drug delivery process. In this embodiment, the device 30 or adapter 34 is programmed to provide an alarm signal if the operational data changes during the process to a point where the data does not match the delivery device control data provided by the handheld computing device 22. If the status signal is STOP, the adapter 34 provides an alarm signal. If the adapter 34 receives a STOP status signal, it does not compare delivery device and patient data. If the adapter 34 determines that the delivery device and patient data match, a green light signal is preferably provided and the adapter 34 continues to run. If the adapter 34 determines that the delivery device and patient data do not match, a red light and alarm are activated. In one embodiment, the adapter 34 sends the alarm signal to the PDA 22.

The system discussed above, including the handheld computing device 22 and the adapter 34, can be programmed to include Neofax information, drug facts and comparisons, American Society of Health-System Pharmacists, and other features such as a dose calculator. Further, a log file of actual infusion data may be kept by the delivery device 30, the adapter 34, or the handheld computing device 22.

Further embodiments may include incorporating oral medications into the patient information data read by the handheld computing device 22, electronic charting (Medication Administration), inputting outcome analysis (e.g., actual pump delivered data, pain scaling, infusion timing data), electronic image capture (e.g., such as for wound care and catheter care), and remote alarm notification to a nurse (via wireless communication). The handheld computing device 22 may be programmed to maintain a log file of patient infusion regimens and communicate the log files through its docking station to an information management system for reporting to the Medication Administration Record (MAR). Other data, which can be captured from the first label 28 on the medication container 26 containing medication information and transferred to the MAR includes container identification, dates of preparation and expiration of the medication, cautions, ordering physician, and prescribed administration route.

Figure 39:
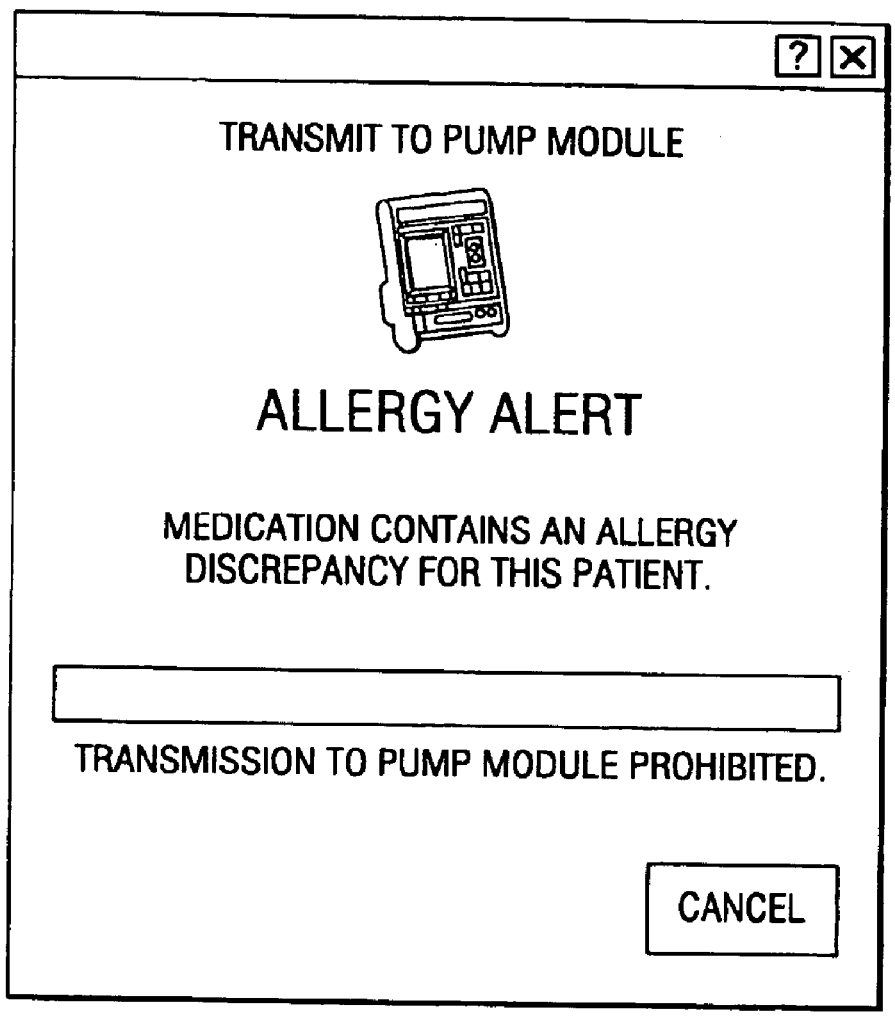

The handheld computing device 22 may further be programmed with patient allergy data and drug compatibility charts. In this embodiment, the handheld computing device 22 determines whether the patient is allergic to the prescribed medication or has been administered a medication previously which is not compatible with the present prescribed medication. As shown in FIG. 39, the handheld computing device 22 is programmed to provide an appropriate warning or discontinue the programming routine if warranted.

Detailed operation of one of many possible embodiments for a series of screen displays on the handheld computing device 22 is shown in FIGS. 2 to 34. In this embodiment, the prescribed medication 27 is an IV drug, the medication container 26 is an IV bag, the patient tag 24 is a bracelet worn at the wrist of the patient, the handheld computing device 22 is a PDA, and the medication delivery device 30 is a programmable electronic IV infusion pump equipped with a programmable adapter 34 (see e.g. FIG. 1). The medication data, medication delivery instruction, and the patient data are provided as two-dimensional data matrix bar codes to be read by a bar code scanner incorporated into the personal digital assistant 22. The communication between the PDA 22 and the electronic infusion pump 30 is via infrared transmission from an infrared transceiver integrated into the PDA 22 and an infrared transceiver 38 connected to the infusion pump 30 via an RS-232 connection.

Figure 2:
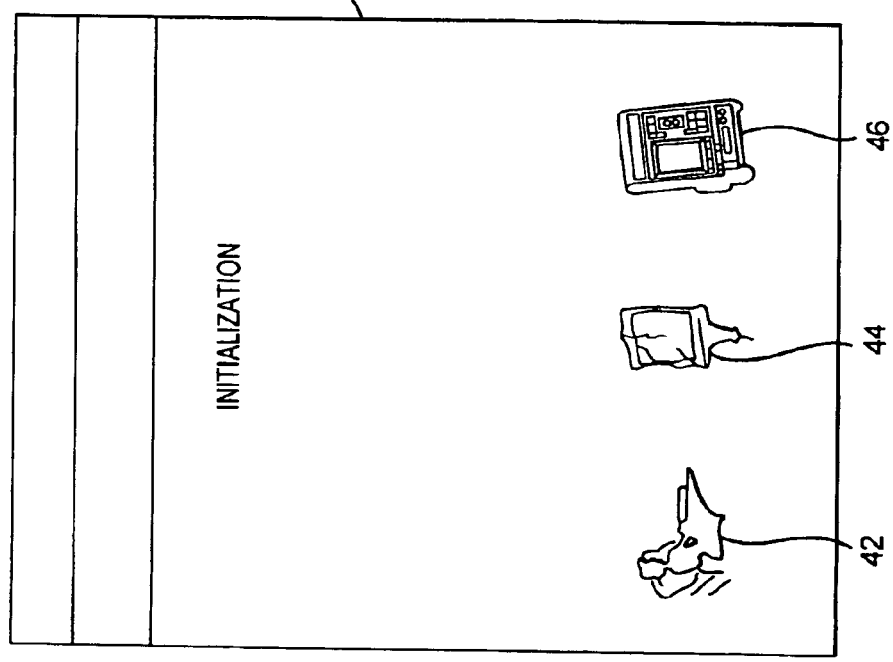

In accord with the present embodiment, FIG. 2 shows an initialization screen of a PDA display 40 having a patient icon 42, an IV icon 44, and a pump icon 46. The initialization screen is generally the first screen displayed on the PDA 22 for programming the system 20 with new patient and medication data. Using a stylus in a manner well known in the art, an operator may enter a patient information mode by tapping or touching the patient icon 42, an IV information mode by tapping or touching the IV icon 44, or a pump mode by tapping or touching the pump icon 46.

If the patient icon 42 is selected, a patient information screen (FIG. 3) is displayed. The patient information screen may include a numerical screen identifier field 50 (a field that may be present on all screens). For example, the numerical screen identifier 001 corresponds to the patient information screen. The patient information screen includes a patient information summary field 48 and a patient icon 42 for proceeding to screen 002.

Figure 3:
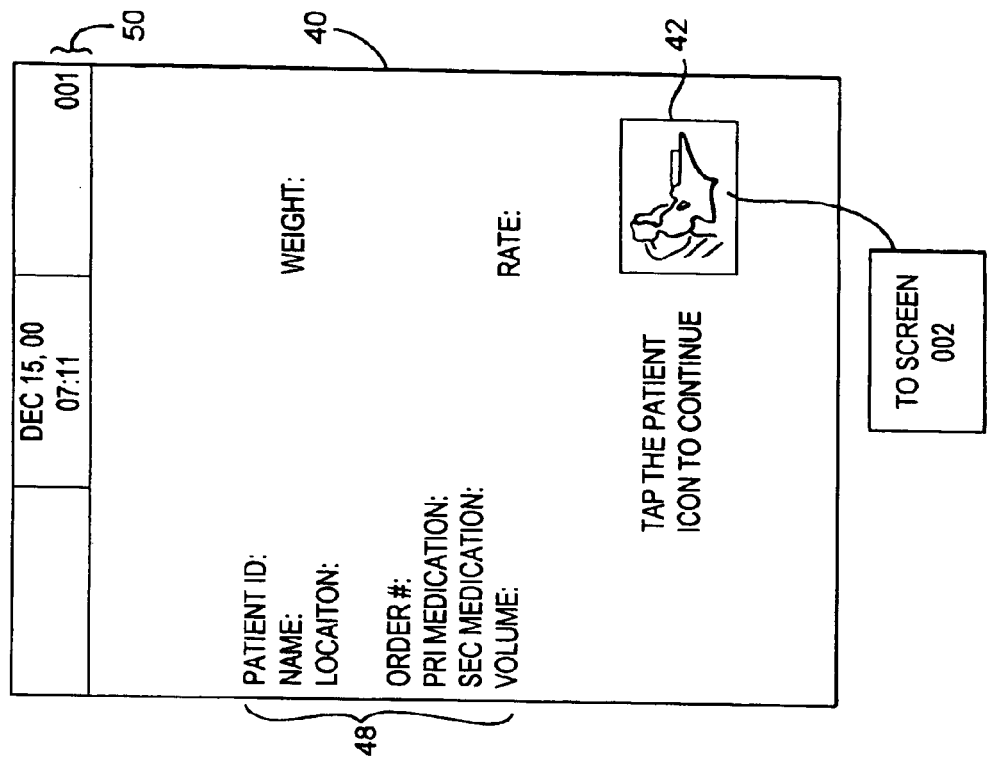
Figure 4:
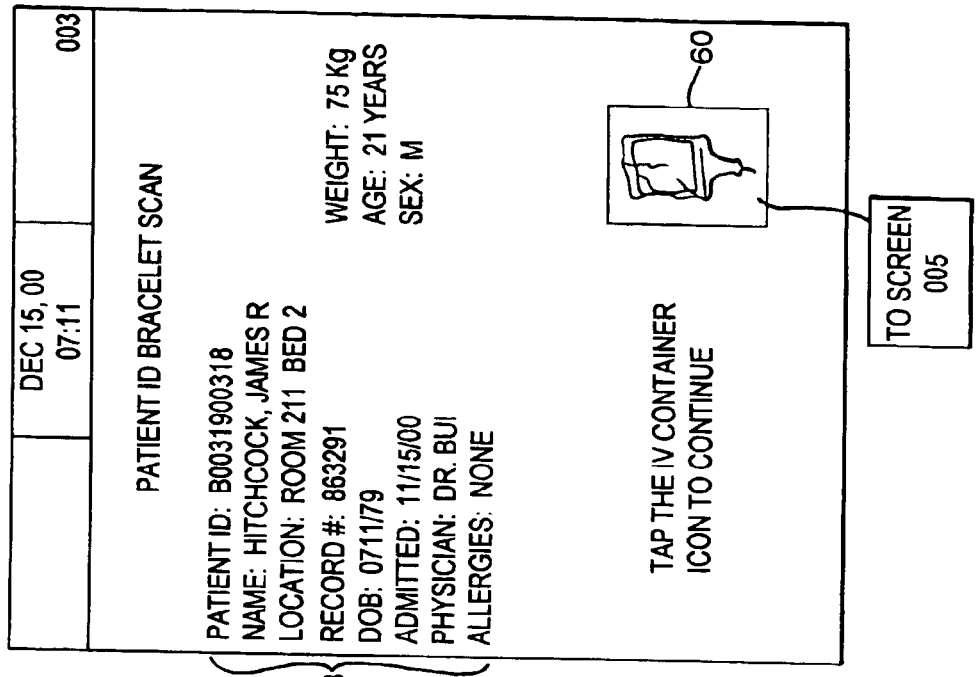

Screen 002 is illustrated in FIG. 4, and includes a display for patient ID bracelet scan soft-key display 52(a) and 52(b). To initiate a bracelet scan, an operator positions the PDA 22 appropriately and depresses either button associated with soft-key 52(a) or 52(b). Screen 002 also includes a help icon and a cancel button. Touching the cancel button returns a user to the patient information screen of FIG. 3. Touching the help icon presents an operator with a bracelet scan help screen (numerical identifier 015), an example of which is shown in FIG. 17.

Figure 5:
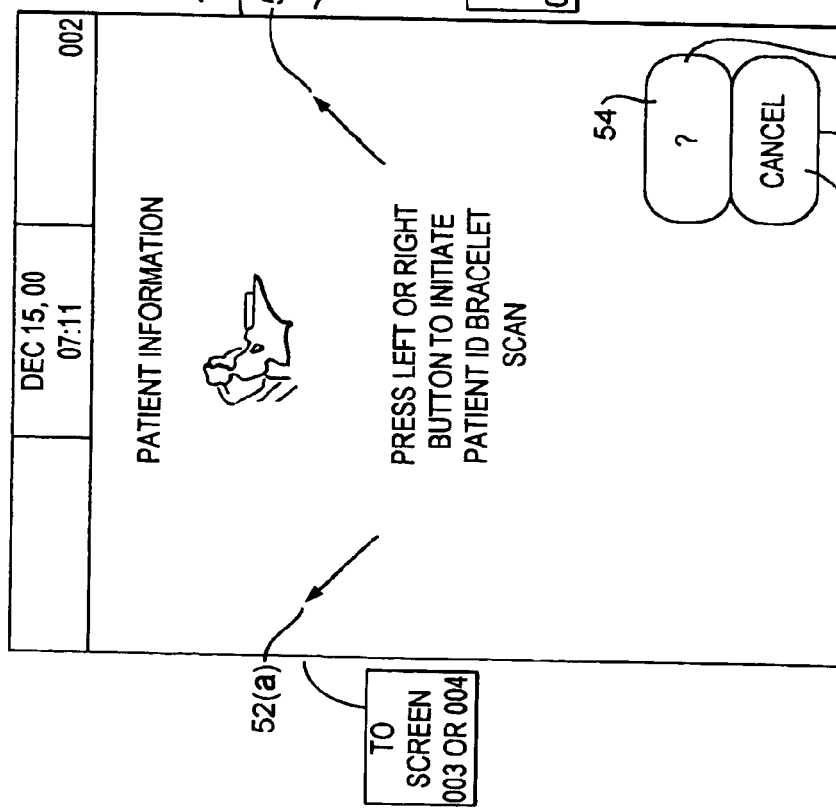

If the patient bracelet scan was successful, the PDA 22 provides a bracelet scan display as shown in FIG. 5, which includes a scan information section 58. The scan information in this display includes the patient identification number, patient name, patient location, medical record number, date of birth, age, date of admission, sex, and the name of the primary physician. Other information can be displayed as desired. The bracelet scan display also includes an IV icon 60 for proceeding to the IV scan page.

In one embodiment, the patient label 29 on the patient bracelet 24 only contains the patient identification number. Detailed patient information is stored in the PDA 22. The PDA 22 scans the label 29 and retrieves and displays the detailed patient information on the PDA 22 as shown in FIG. 5

If the bracelet scan was not successful, the PDA displays the screen as shown in FIG. 6. This screen includes a soft-key display 62(a) and 62(b) for reinitiating a scan, a help icon 64 for jumping to an unsuccessful scan help page such as that shown in FIG. 21, and a cancel button 66.

FIG. 7 shows an IV container scan initiation display. The display has a soft-key display 68(a) and 68(b), as well as a help icon 70 for jumping to an IV container information help display page, shown in FIG. 19. A cancel button 72 is also included for returning to the bracelet scan successful display shown in FIG. 5. To initiate a container scan, the operator positions the PDA 22 appropriately and depresses either button associated with the soft-key 68(a) or 68(b)

If the IV scan was successful, the PDA 22 provides an IV scan display as shown in FIGS. 8(a) and 8(b), which includes a scan information section 74. The scan information in these display pages includes patient identification number, patient name, patient location, patient weight, order number, bag identification number, medication identification, volume, and rate, medication preparer's name and the date and time the preparation was completed, the expiration time and date, the delivery time and date, the administration route. The display could also include an identification of the individual that hung the IV and the date and time the IV was hung. The IV scan display also includes a pump icon 76 for proceeding to the pump page.

Figure 9:
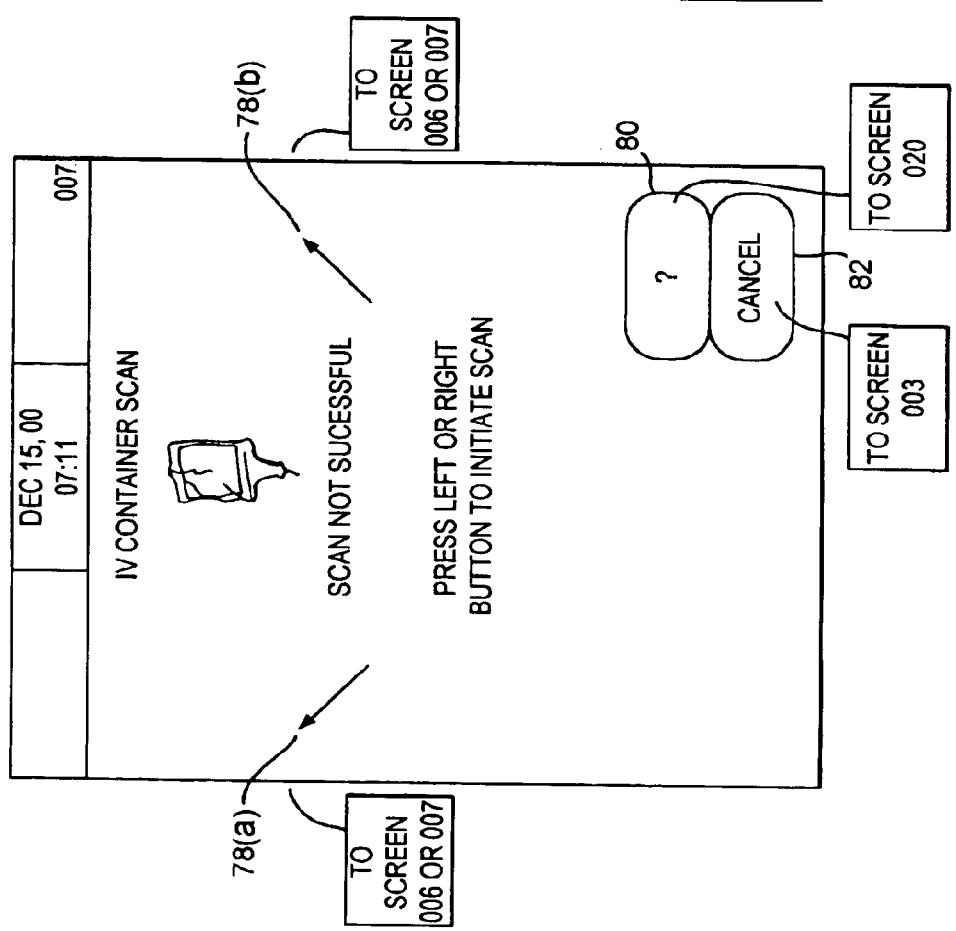

If the IV scan was not successful, the PDA displays the screen as shown in FIG. 9. This screen includes a soft-key display 78(a) and 78(b) for reinitiating a scan. A help icon 80 for jumping to the unsuccessful IV scan display shown in FIG. 22, and a cancel button 82 are also included.

Figure 10:
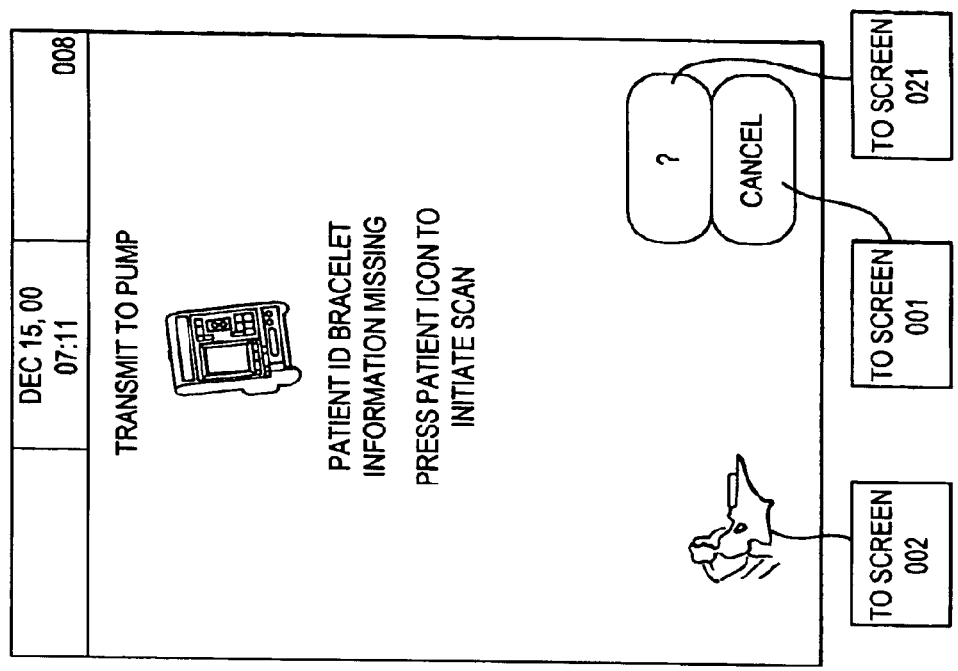
Figure 11:
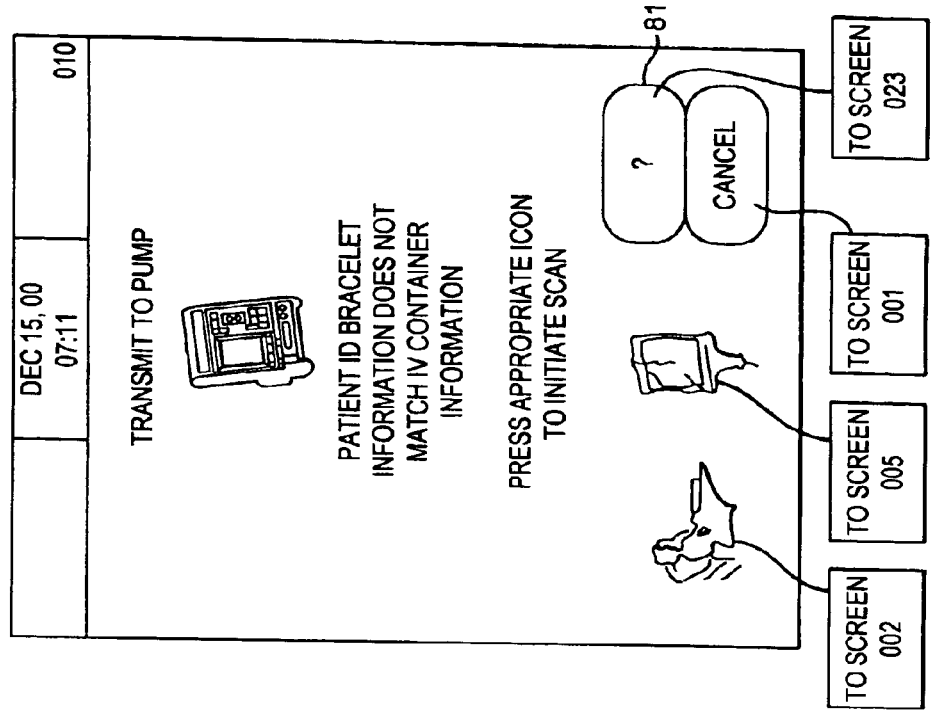

If the IV scan was successful, but either patient information or IV information is missing from the PDA database, the PDA 22 provides the display shown in FIG. 10 or FIG. 11. Both screens advise of the information that is missing and allow the operator to move back to the respective scan initiation page, jump to a respective help page or cancel the programming sequence. The respective help pages, shown in FIGS. 23 and 24, advise the operator of the problem and the manner of correction.

Figure 12:
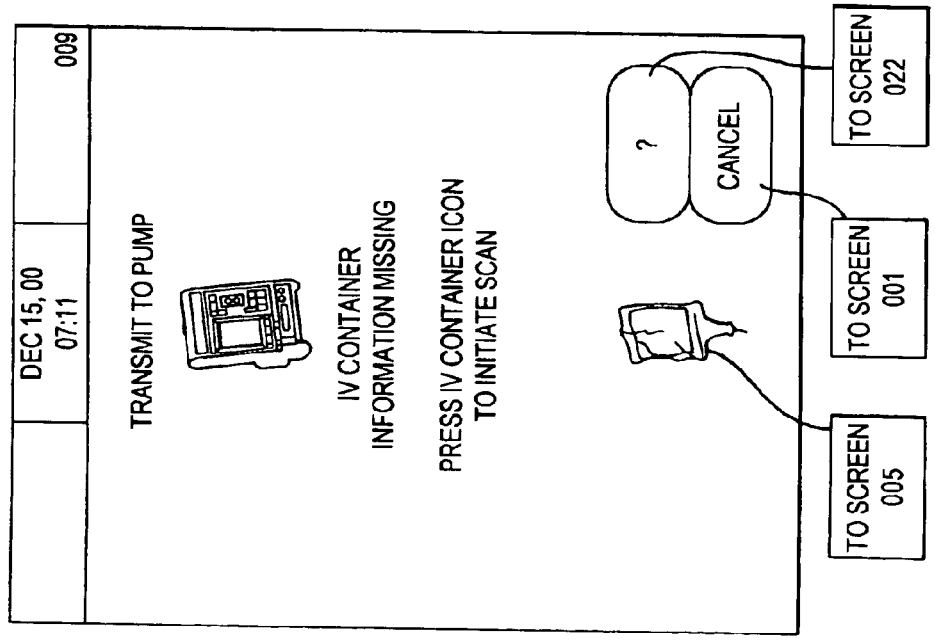
Figure 13:
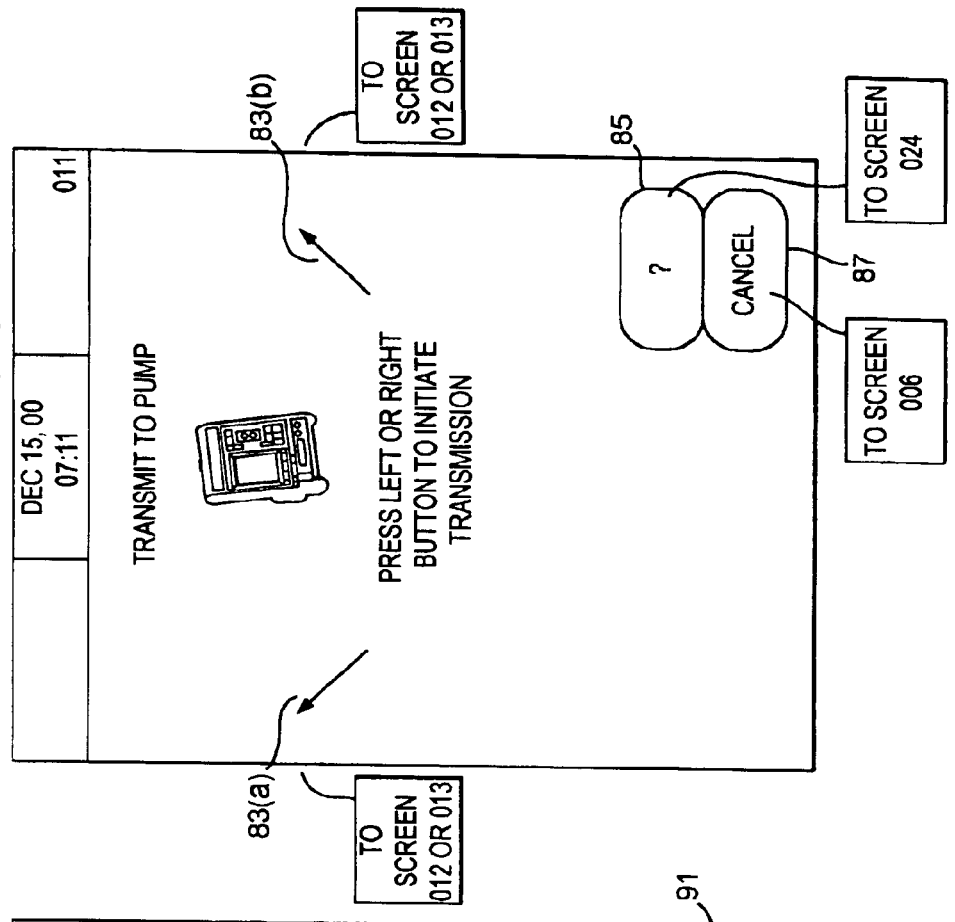

If the IV scan was successful, but the patient information does not match the IV information, the PDA 22 provides the display shown in FIG. 12, allowing the operator to jump back to the display for scanning the patient bracelet label 29 or the IV container label 28. This display also has an icon 81 for jumping to the help screen shown in FIG. 25, which explains that the information does not match and the bar codes 28 and 29 should be rescanned.

If a match between the medication data and patient data is confirmed, the PDA 22 displays a manual confirmation screen as shown in FIG. 13(a). After the operator confirms the data match, the operator, by pushing the button 91, can advance to the medication delivery information screen shown in FIG. 13(b). The medication delivery screen in FIG. 13(b) includes soft-keys 83(a) and 83(b). The operator positions the PDA 22 appropriately close to the pump 30 and depresses either button to initiate the transmission of the medication delivery information from the PDA 22 to the pump 30 via the second communication device 38 integrated with or connected to the medication delivery device 30, or via the adapter 34 in embodiments with the adapter 34. The PDA medication delivery transmission display also includes a help icon 85 for jumping to the display shown in FIG. 26, which instructs the operator regarding the transmission of prescription information from the PDA 22 to the pump 30, and a cancel icon 87, which return to the IV container scan page as shown in FIG. 8(a).

Figure 14:
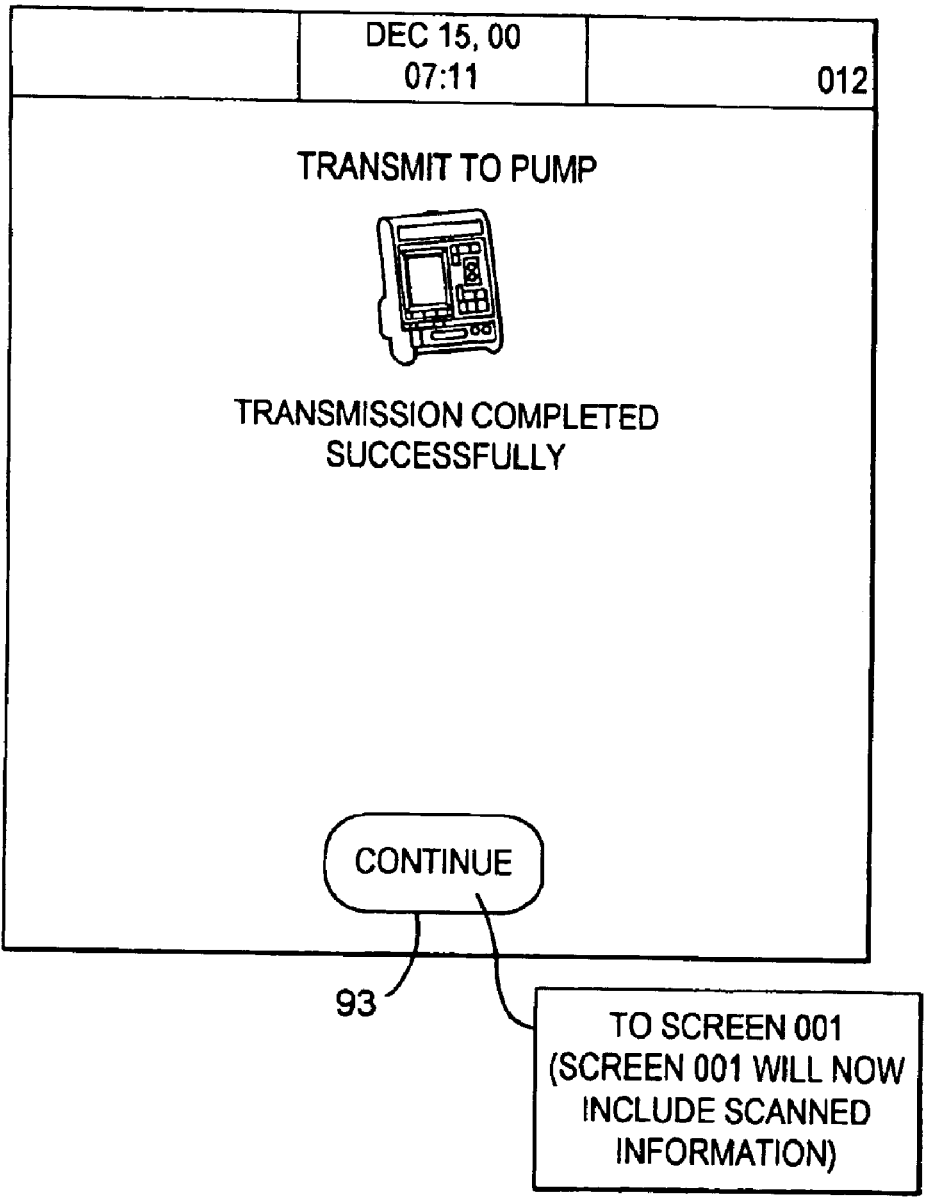

If the medication delivery information was transmitted successfully, the display of FIG. 14 is shown on the PDA 22, and the operator may jump to screen 001 by pressing the continue display icon 93 on the touch-screen, and the PDA 22 will provide the display of FIG. 3, or a similar display depending on the application or other specifics, with information in each field. Examples of displays provided in response to successful transmission of prescription information are shown in FIGS. 16 and 18.

If the medication delivery information was not transmitted successfully, the PDA 22 will display one of a number of messages indicative of whether an error was detected, and if so the cause of the error. If the infrared transmission was incomplete, the display of FIG. 15(a) is shown on the PDA 22, and the operator may press the activation button 95(a) or 95(b) to retransmit. The display also includes a help icon 97 for jumping to the display shown in FIG. 27, which explains potential causes for the transmission error. The display further includes a cancel button 99 for returning to the display of FIG. 8.

If the PDA 22 transmitted the medication delivery information, but did not receive a confirmation from the pump, the display of FIG. 15(b) will be shown. The display of FIG. 15(b) includes a help button for jumping to the help display of FIG. 15(c). This help display 101 in the display of FIG. 15(b) informs the operator of potential problems that may cause the pump to be non-responsive. The operator may then correct the problem and return to the transmit screen by pressing the "OK" button 103.

Figure 15D:
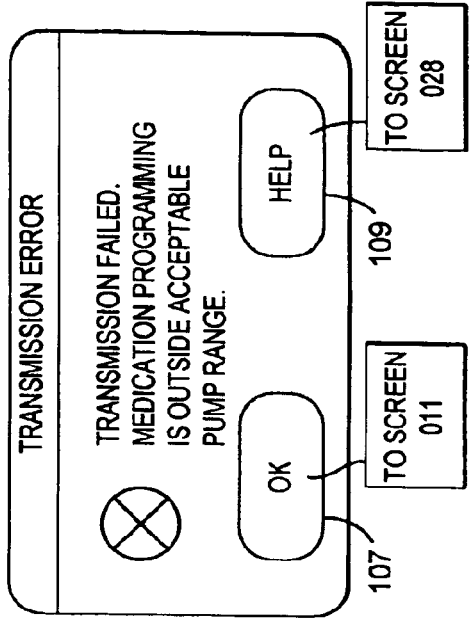
Figure 15C:
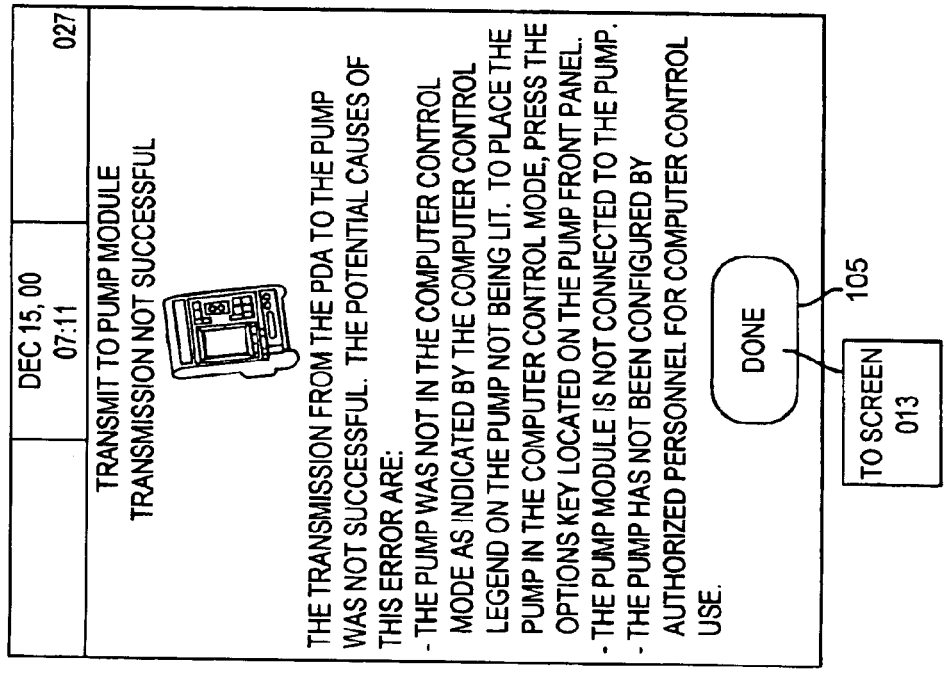

If the medication delivery information includes data that is outside of the acceptable parameters for the pump, the display of FIG. 15(d) is shown on the PDA 22. A help screen is provided (FIG. 15(e)) for instructing the operator to correct a parameter when the help button 109 is depressed. The operator may jump back to the transmission page by pressing the "OK" button 107.

Figure 15F:
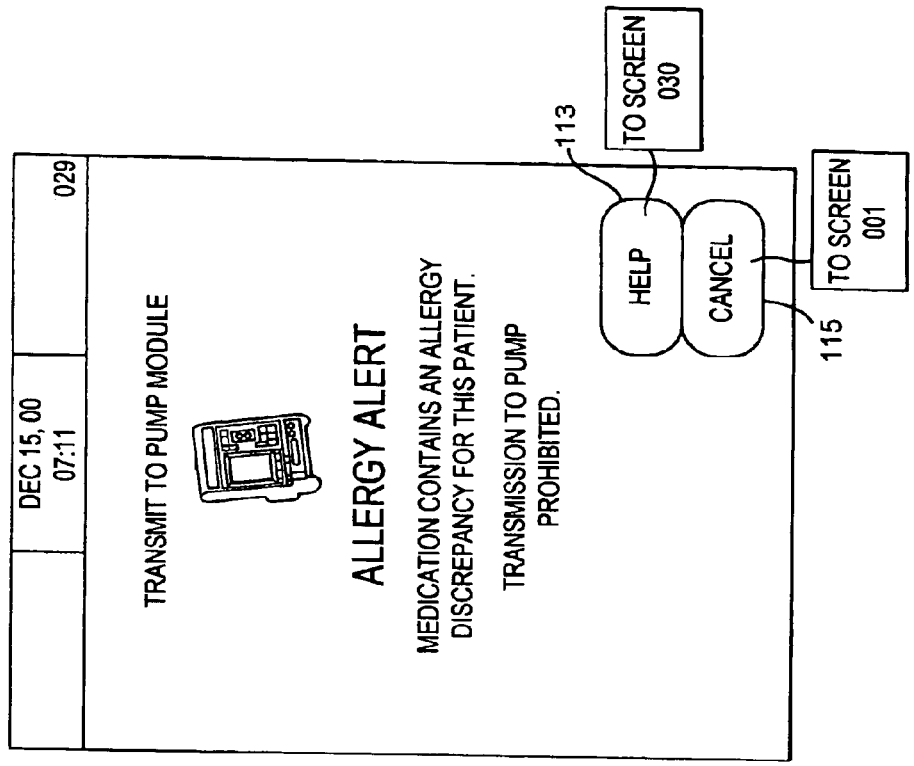
Figure 15E:
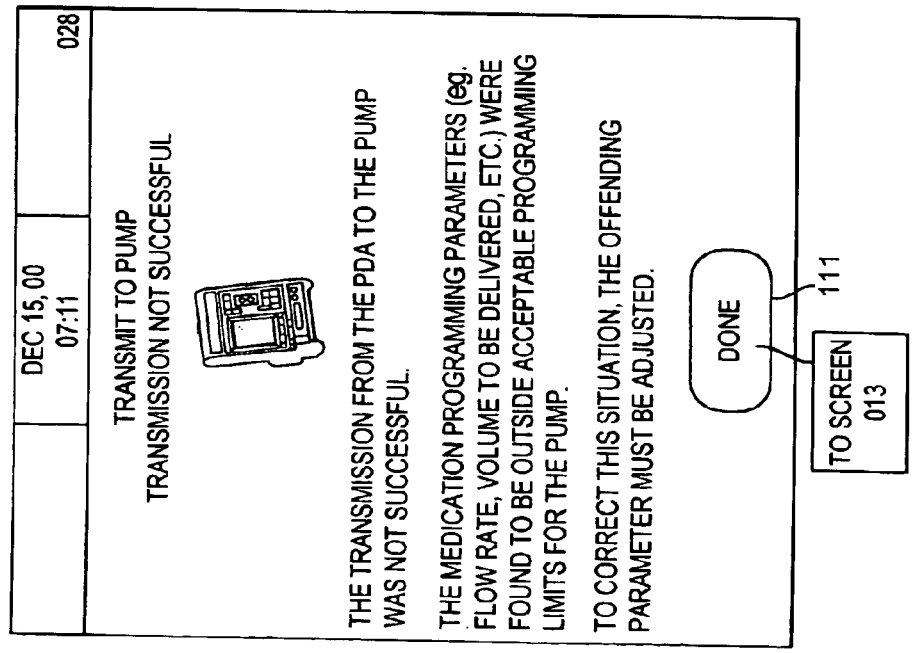

If the PDA 22 reviews the medication delivery information against the patient allergy data and finds that the medication contains an allergy discrepancy for the patient, the transmission error display of FIG. 15(f) will be shown. The operator may jump to the help screen shown in FIG. 15(g) by depressing the help button 113 for a further explanation of the allergy conflict or exit the present programming string by depressing the cancel button 115.

Figure 15J:
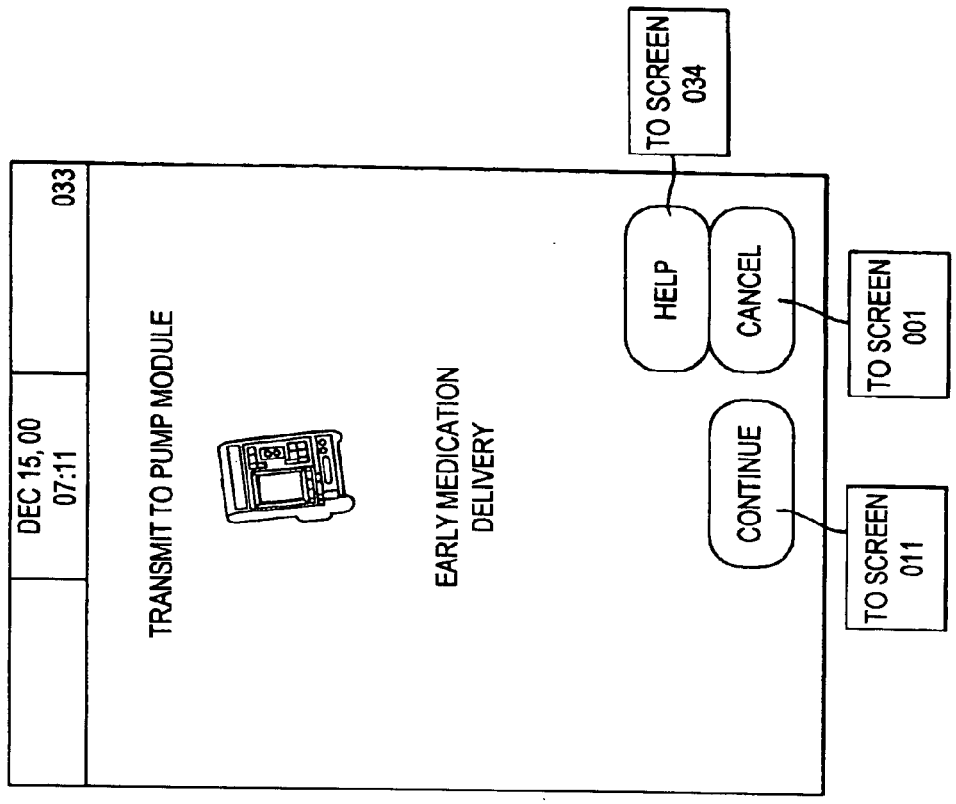
Figure 15I:
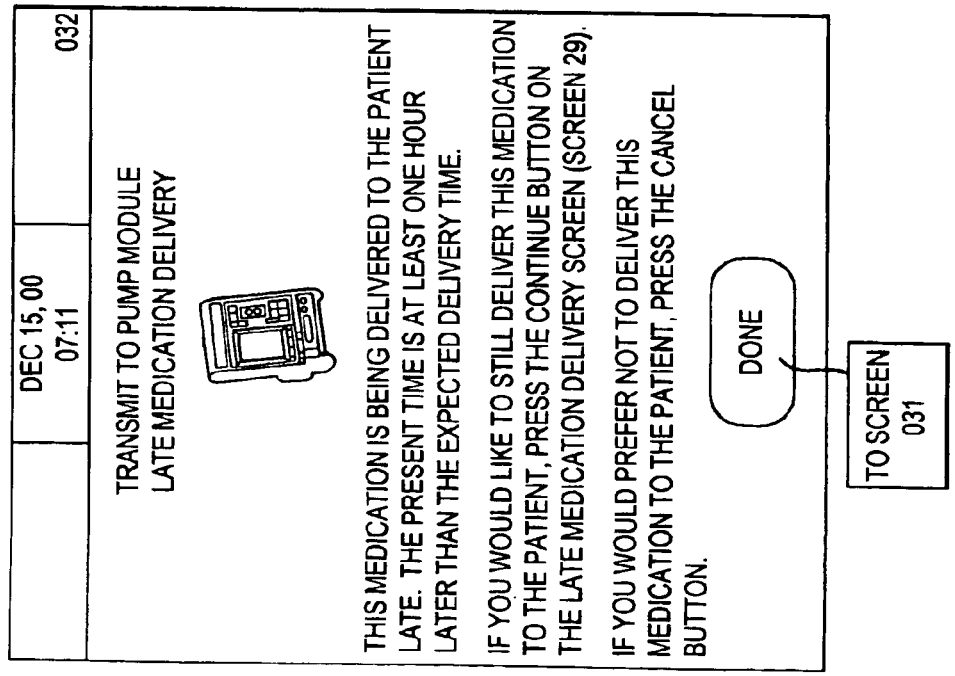
Figure 15K:
Figure 21:
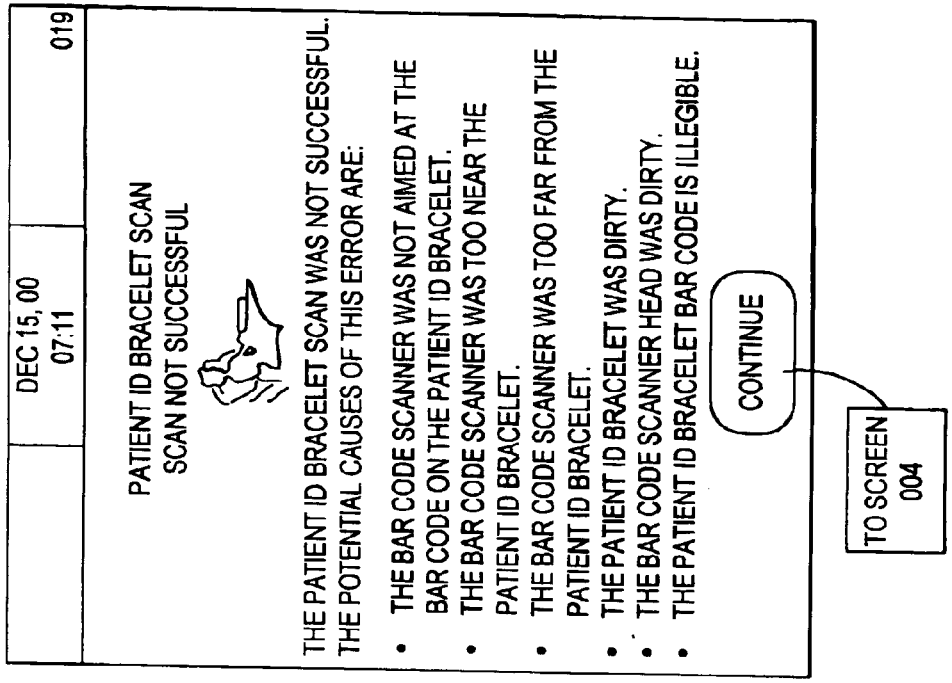

Additional reasons that may cause the PDA 22 to not immediately proceed with programming the pump are that the medication is being delivered too late and that the medication is being delivered too early. FIGS. 15(h) and 15(j) show the late and early medication delivery displays, respectively. Associated help pages (FIGS. 15(i) and 15(k)) may be accessed to display the specifics of the drug delivery attempt time with respect to the prescribed regimen.

Figure 20:
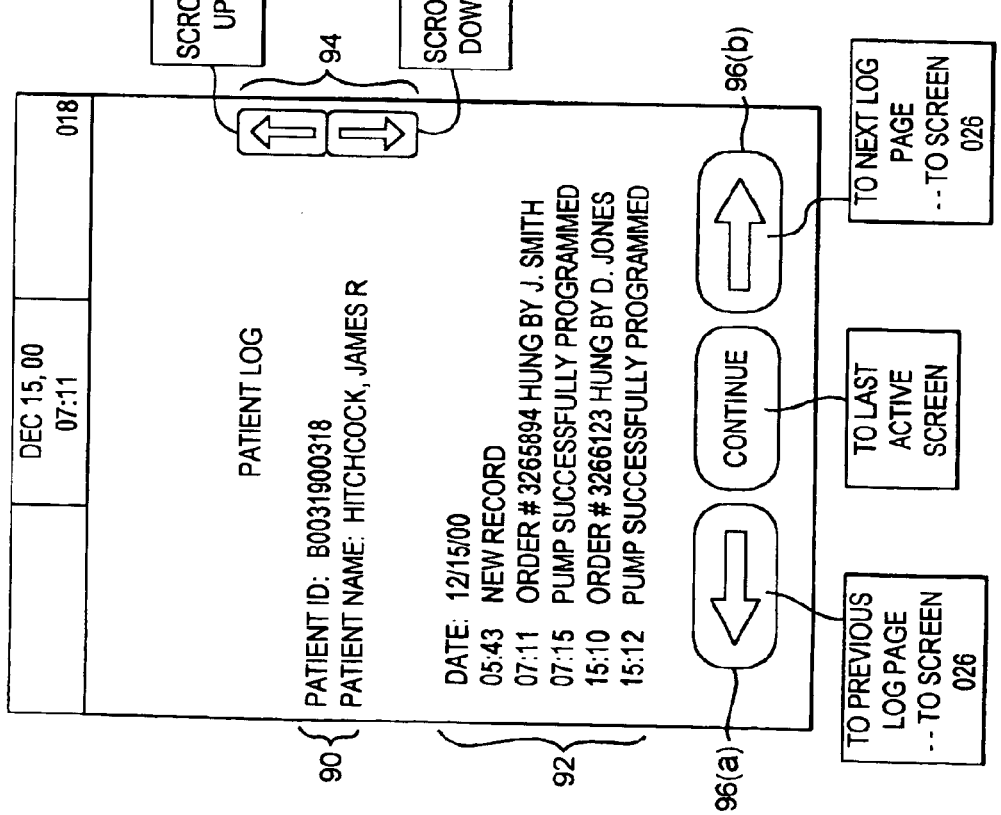
Figure 23:
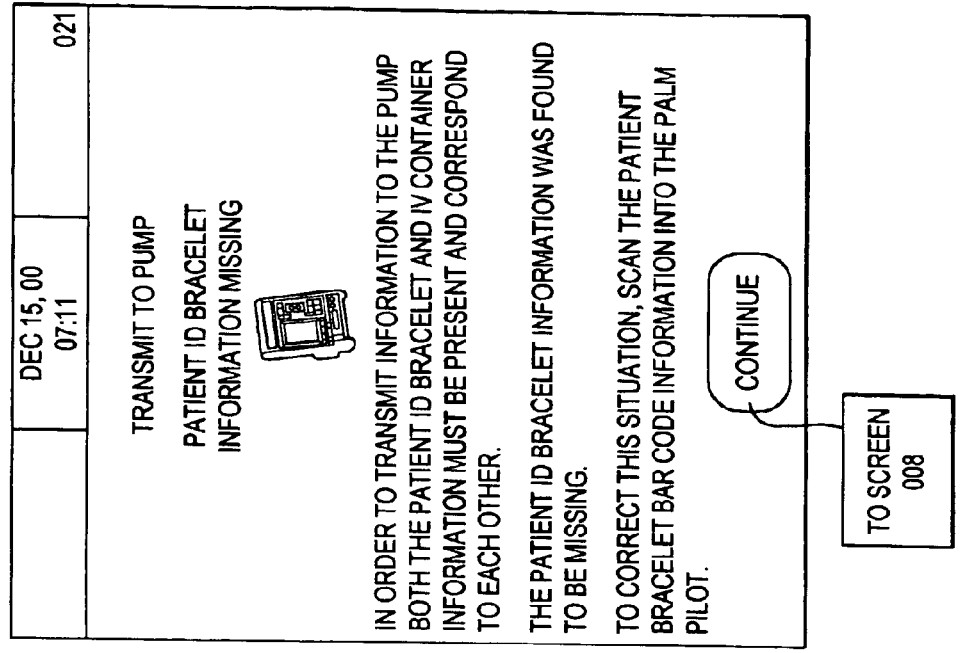
Figure 22:
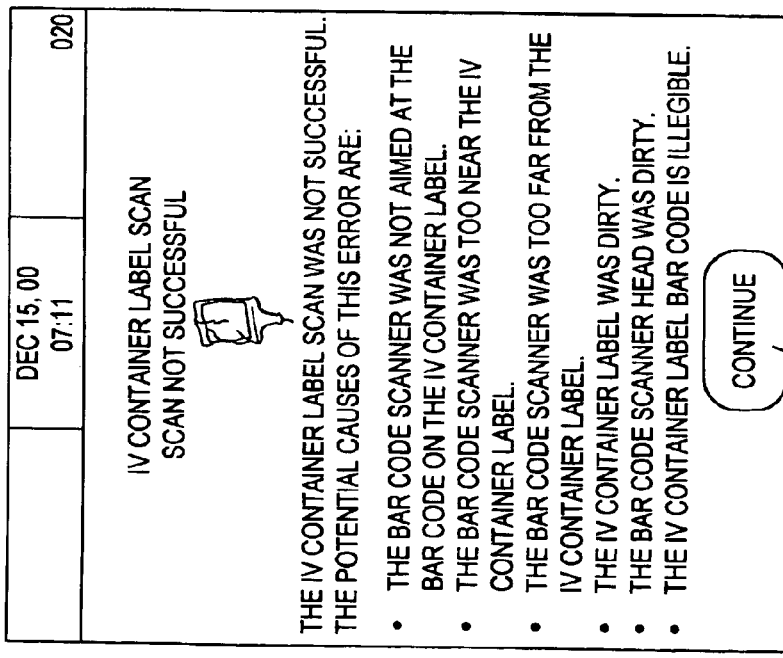
Figure 24:
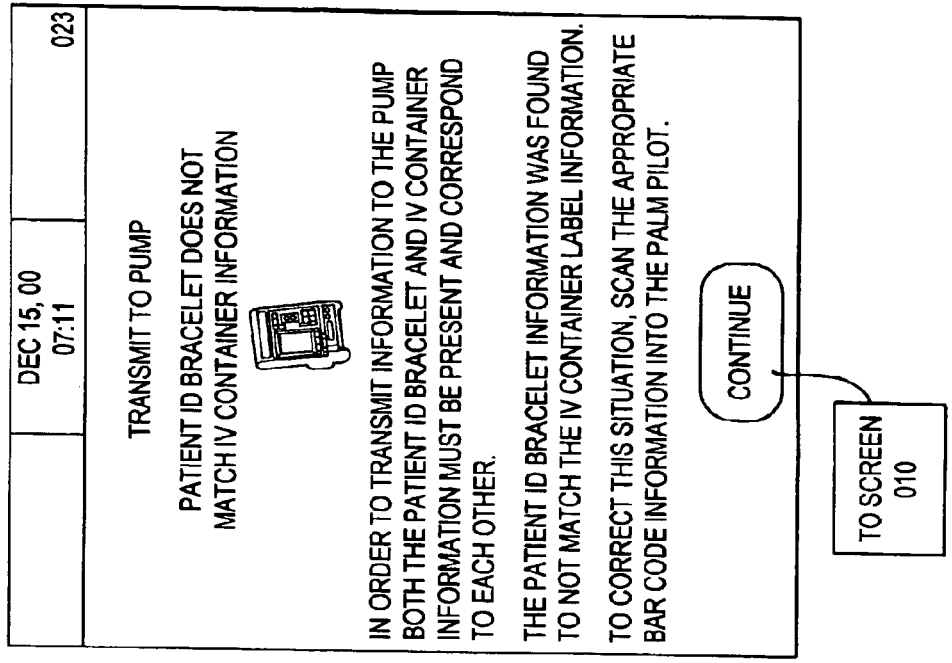
Figure 25:
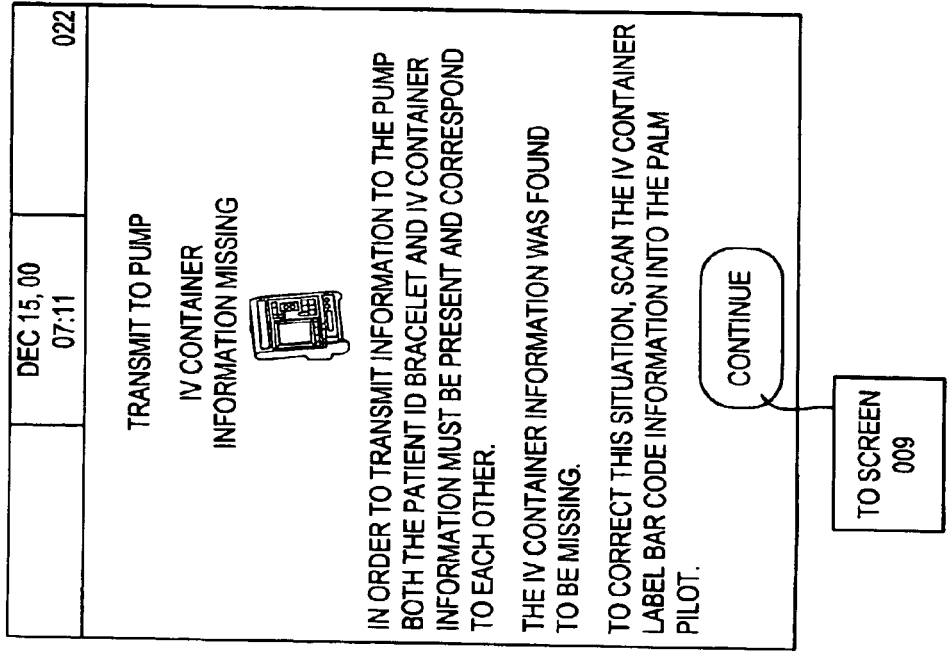
Figure 26:
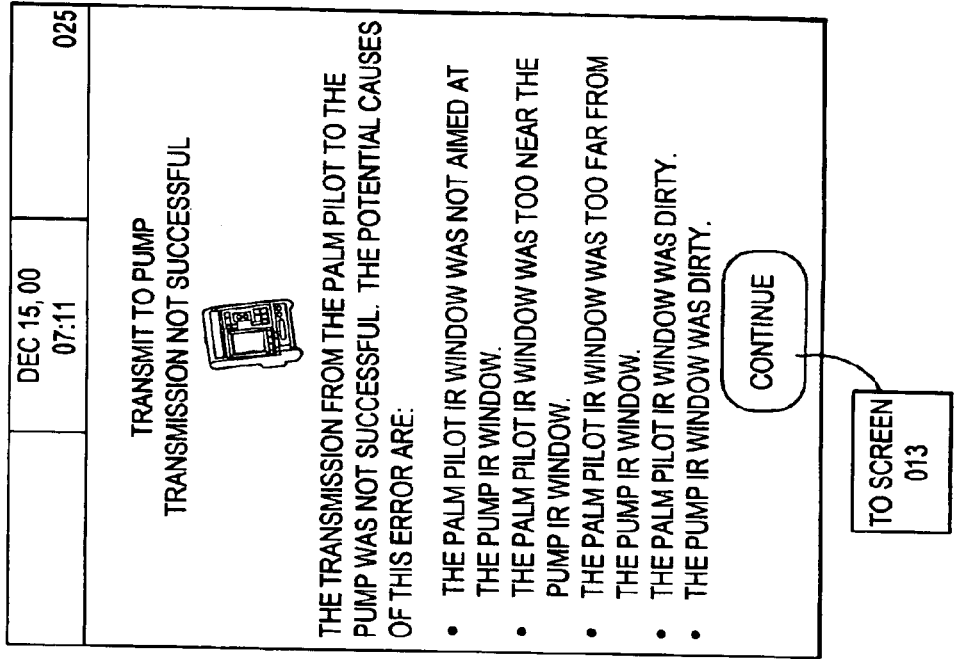
Figure 27:
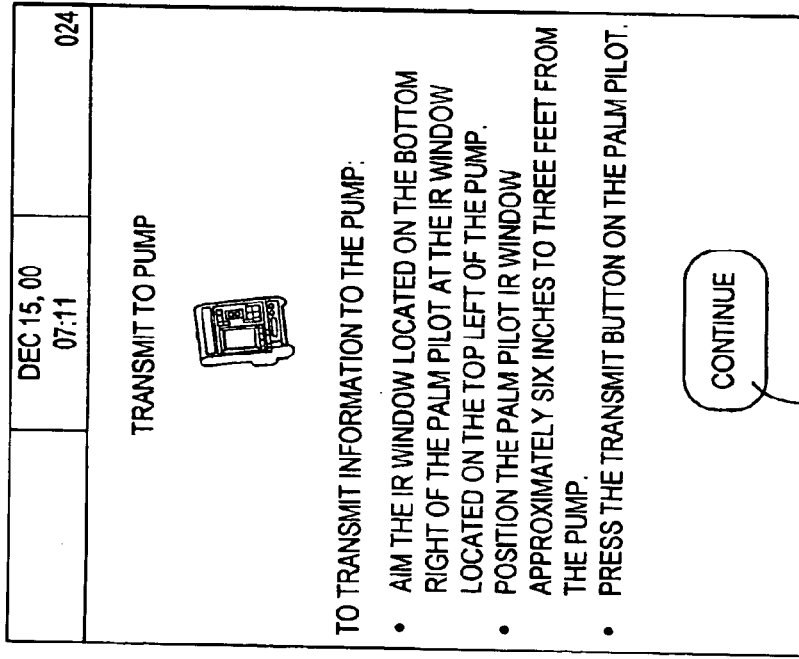
Figure 30B:
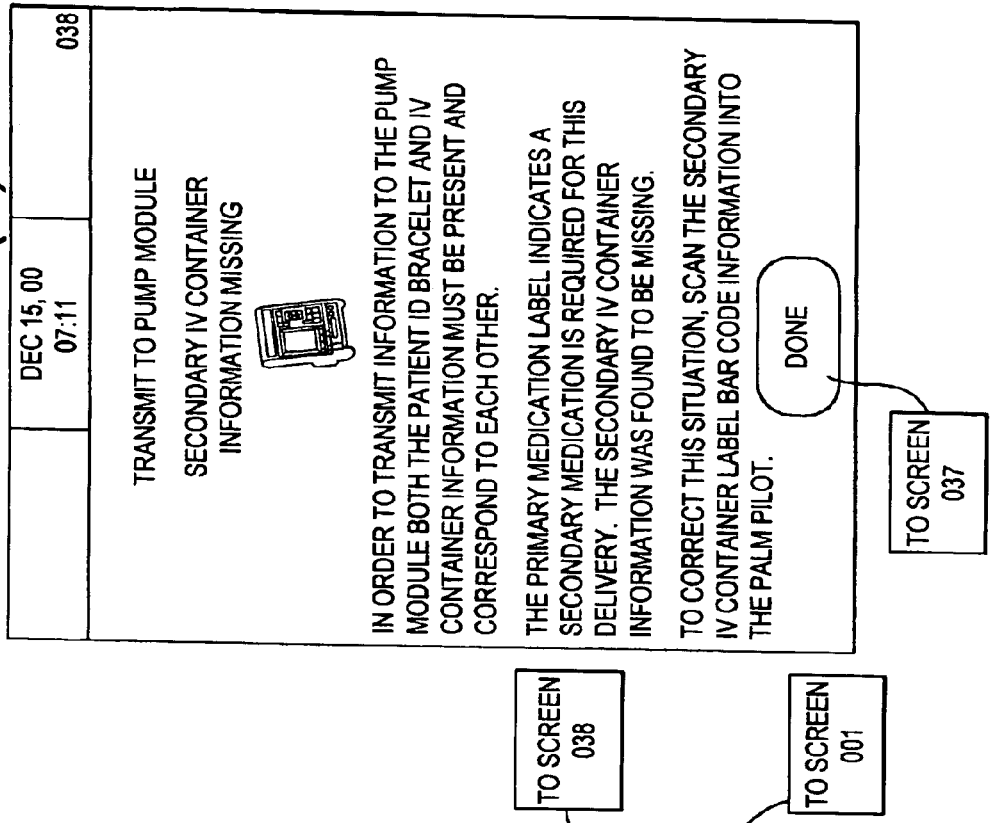
Figure 30A:
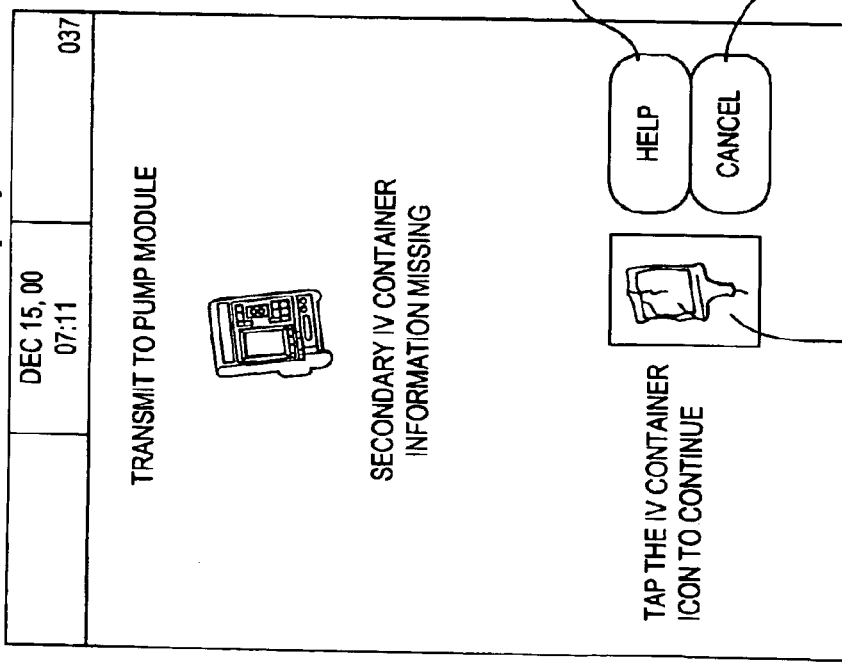
Figure 31B:
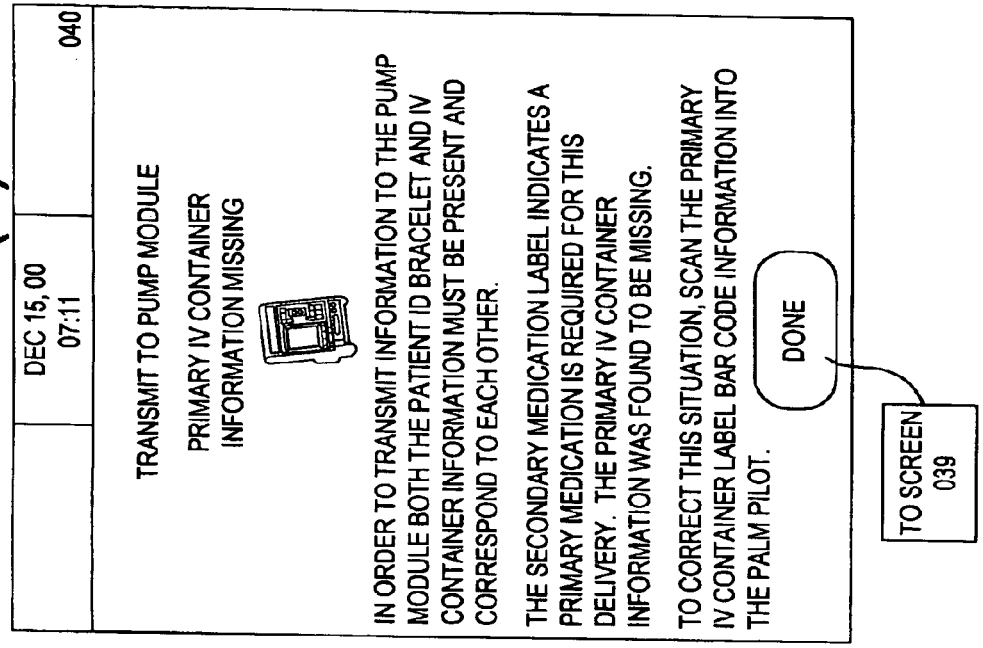
Figure 31A:
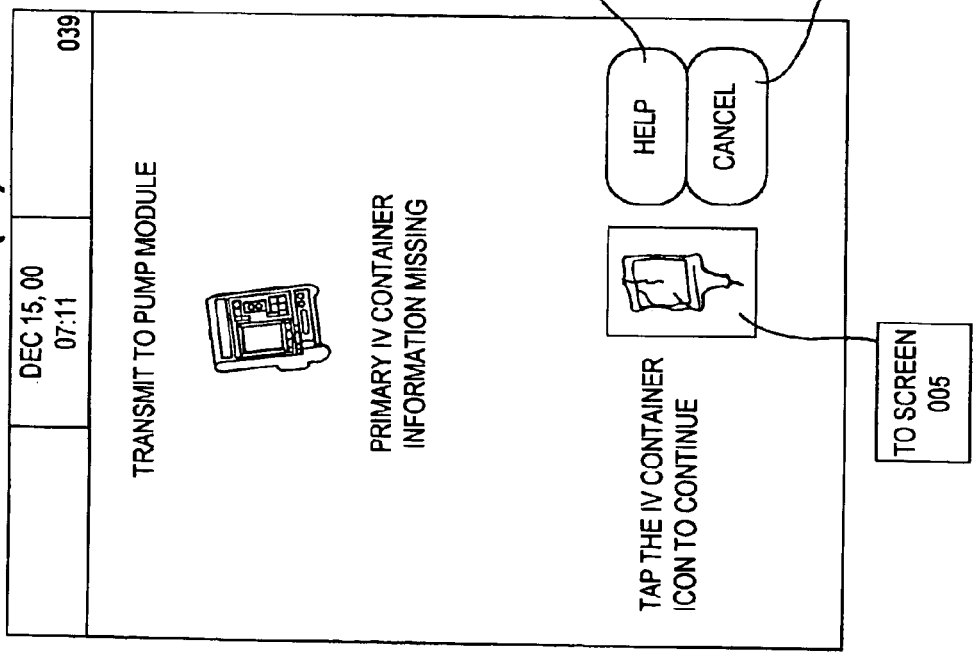

As discussed above, the PDA 22 may also be configured for accessing a patient log. An example of a patient log display is shown in FIG. 20. This display includes a patient identification field 90 and a patient activity field 92. As shown, the patient activity field 92 includes the date and time of activities related to patient infusions listed sequentially. Scroll buttons are provided on the display for progressing to later or earlier times or dates, if applicable. Also, if multiple log pages are existent, an operator may navigate through log pages using previous and next navigation buttons 96(a) and 96(b). If additional log pages do not exist, the PDA displays such a message, as shown in FIG. 28.

The PDA 22 may also retain a record of daily transactions and download the record to an information system, locally at the nursing station or to the central pharmacy computer system, so as to maintain the MAR record electronically verses manually. In one embodiment, the PDA is equipped with a 2D bar code reader having a CCD imager and can capture signatures or other photographic evidence electronically. The PDA 22 may include software to provide the allergy database, drug compatibility charts, and drug handbooks.

The PDA 22 may also include display for programming the pump to administer two or more medications simultaneously. Referring to FIG. 29(a), therein is shown page 1 of a secondary medication data page. FIG. 29(b) shows page 2 of a secondary medication data page. The secondary medication pages identify the patient and also include fields for displaying information regarding specifics of the secondary medication, as well as buttons for jumping to the displays that provide for reading the secondary IV label. FIGS. 37 and 38 show screen displays associated with a multiple medication configuration. As shown in FIG. 37, the desired medications are selected. In FIG. 38, the primary and secondary medications are selected.

FIGS. 30(a), 30(b), 31(a), and 31(b) show the displays, and respective help displays, shown when the PDA 22 has not received all of the secondary or primary IV information. FIG. 32(a) shows the display provided if the primary and secondary IV information do not correspond to one another. FIG. 32(b) shows the corresponding help page.

Figure 34A:
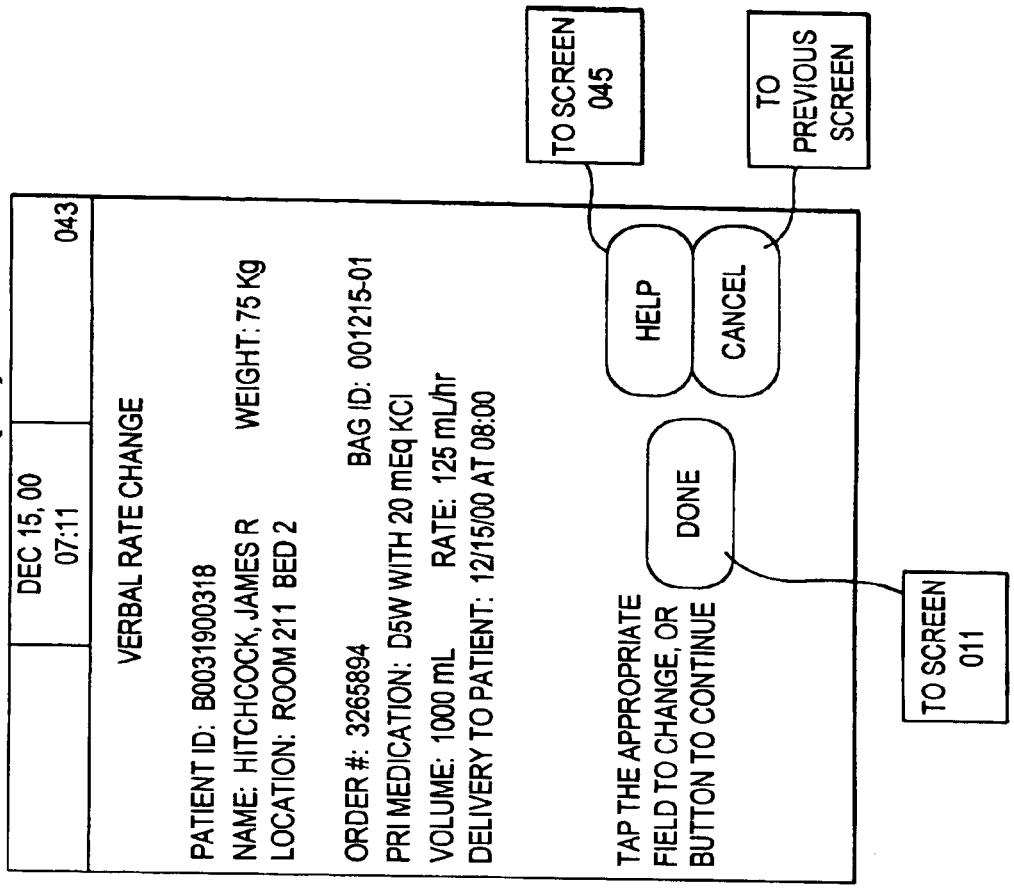
Figure 33:
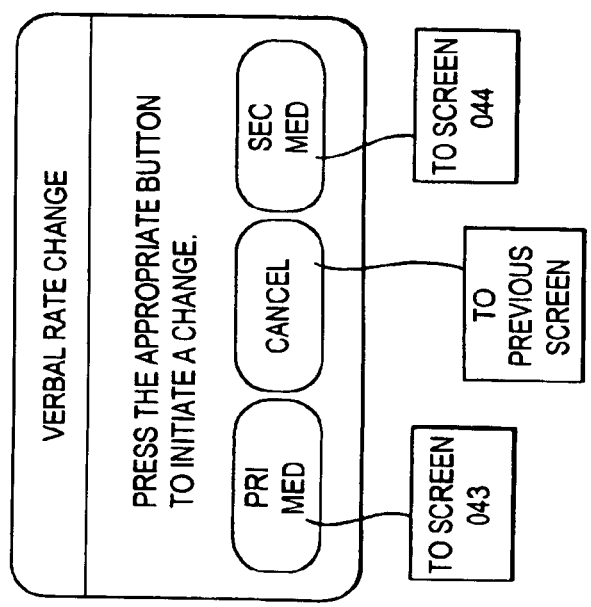

FIG. 33 shows a display presented to allow an operator to change the flow rate or volume field data in the PDA 22. An operator taps the "PRI MED" button to jump to the primary medication verbal rate change display of FIG. 34(a) and taps the "SEC MED" button to jump to the secondary medication verbal rate change display of FIG. 34(b). FIG. 34(c) shows the help display provided for each verbal rate change display.

Figure 35:
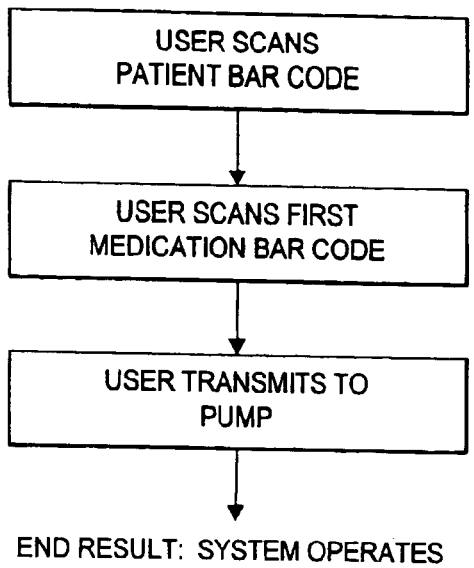
FIG. 35 is a flow chart showing several steps for scanning a single medication.
Figure 36A:
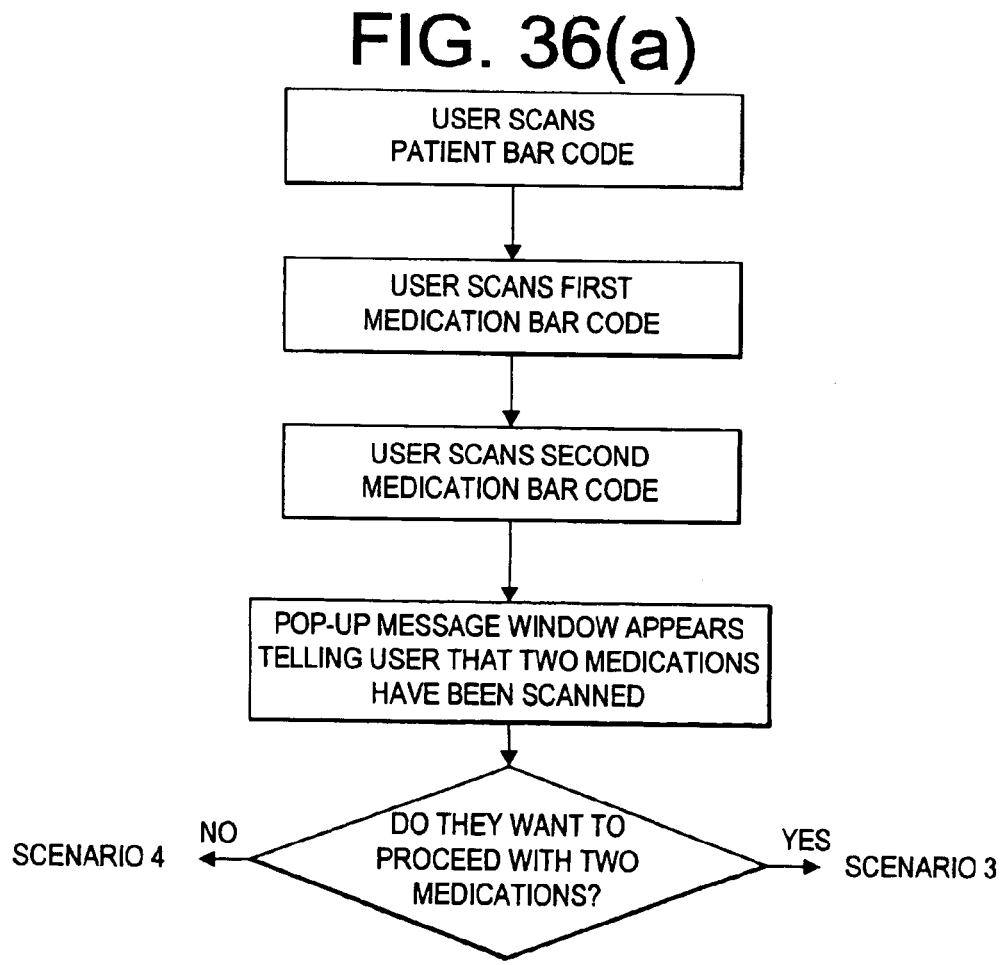
FIGS. 36(a)–36(c) are flow charts showing several steps for scanning two medications.
Figure 36B:
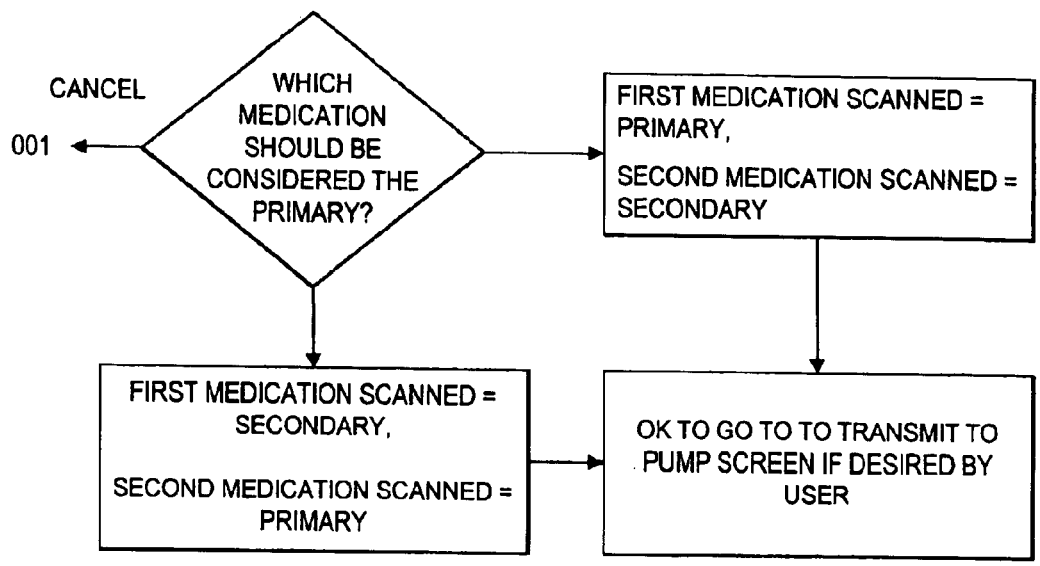
Figure 36C:
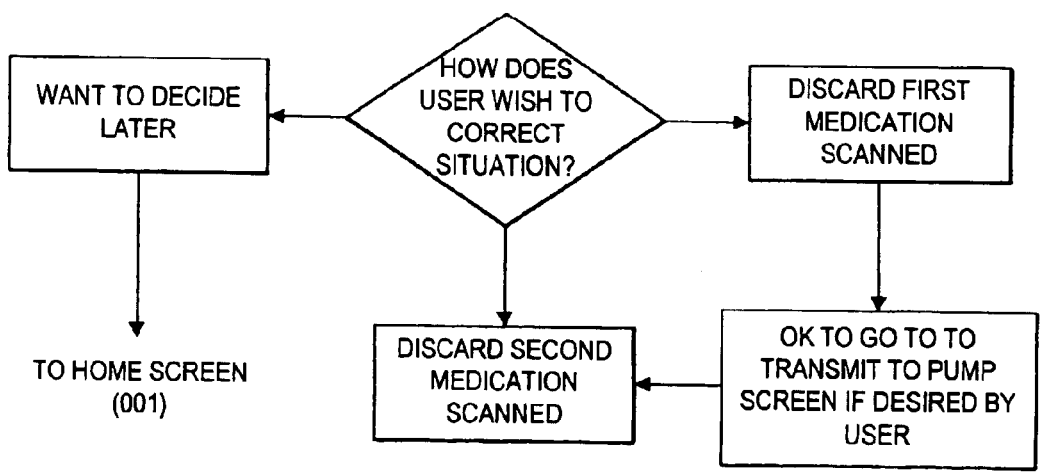

FIG. 35 is a flow chart for processing bar code information to a pump using the PDA 22 for programming the pump with one medication. FIGS. 36(a)–36(c) show the flow charts for programming the pump with two medications. Referring to FIG. 36(a), the PDA 22 automatically prompts the operator after two medication bar codes have been scanned. Referring to FIG. 36(c), if the operator does not wish to proceed with two medications, the PDA 22 displays a series of option menus for proceeding with either the first or second scanned medication, or returning to the initial screen. Referring to FIG. 36(b), if the operator wished to proceed with two medications, the PDA 22 prompts the operator to indicate which medication is to be the primary and which is to be the secondary. The operator may also cancel the programming of the pump at any time thorough appropriate button selection. In one embodiment, the operator may scan the bar code 39 on the catheter 37 by the scanning device 36 on the PDA 22 to confirm that the medication 27 is being delivered to the patient via the correct catheter 37. The operator may also scan the bar code 31 on the pump 30 by the scanning device 36 on the PDA 22 to confirm that the proper pump channel is being used if a multi-channel pump is utilized.

The system of the present invention provides a method generally comprising the following steps. First, a medical provider such as a nurse scans the patient bracelet 24 with the PDA 22 and captures the data listed above. The nurse then scans the IV bag label with the PDA 22 and captures the corresponding data listed above. Having received the data, the PDA 22 reports a match or mismatch of the patient bracelet 24 data with the IV bag 26 data. If a match is confirmed, the nurse then downloads the data received from the patient bracelet label 29 and the IV bag label 28 to the infusion pump 30 via the second communication device 38 integrated with or connected to the medication delivery device 30, or via the adapter 34 in embodiments with the adapter 34. The infusion pump 30 is subsequently enabled to implement that program according to the instruction downloaded from the IV bag label 28. The pump 30 or the adapter 34 sounds an alarm if the delivery rate, drug dose, or drug is subsequently altered from the downloaded data.

The benefits of the medication delivery system in the present invention are significant. At the present time, medication delivery such as IV infusion is driven by a manual set up and verification process, resulting in a significant number of human errors reported each year. The described system reduces such errors by verifying that the right drug is given to the right patient, in the right dose at the right time. The system further prompts a clinician nurse to verify the right route of delivery, and can be further enabled to identify the correct route by using a bar code or RFID tag on the delivery catheter.

It is understood that, given the above description of the embodiments of the invention, various modifications may be made by one skilled in the art. Such modifications are intended to be encompassed by the claims below.

What is claimed is:

1. A medication delivery system capable of communicating and matching prescribed medication data from a first label on a medication container holding the medication and patient data from a second label on a tag adapted to be worn by a patient wherein the first label also containing instruction of delivering the medication, and the medication and patient data being provided in machine readable formats, the medication delivery system comprising:
   (a) a medical device in communication with the medication container, the medical device adapted to delivering the medication from the container to the patient, the medical device having a data port for receiving information; and
   (b) a handheld computing device having means for reading the prescribed medication data and the patient data and comparing the data to confirm a match between the medication data and patient data, the handheld computing device having a transmitter capable of transmitting the medication delivery instruction from the handheld computing device to the medical device wherein the medical device is adapted to deliver the medication to the patient according to the instructions.

2. The medication delivery system of claim 1 wherein the handheld computing device is a personal digital assistant.

3. The medication delivery system of claim 1 wherein the machine readable data of the prescribed medication and the instruction of delivering the prescribed medication are coded in a format selected from the group consisting of: linear bar codes, two-dimensional bar codes, printed data encoding technology, radio frequency identification technology, magnetic stripes or tapes, optical character recognition technology, and optical holograms.

4. The medication delivery system of claim 1 wherein the machine readable prescribed medication data and medication delivery instruction are coded in two-dimensional bar codes.

5. The medication delivery system of claim 1 wherein the machine readable patient data is coded in a format selected from the group consisting of: linear bar codes, two-dimensional bar codes, printed data encoding technology, radio frequency identification technology, magnetic stripes or tapes, optical character recognition technology, and optical holograms.

6. The medication delivery system of claim 1 wherein the machine readable patient data is coded in two-dimensional bar codes.

7. The medication delivery system of claim 1 wherein the first label of medication data is a two-dimensional bar code integrated with text.

8. The medication delivery system of claim 1 wherein the second label of patient data is a two-dimensional bar code integrated with text.

9. The medication delivery system of claim 1 wherein the first label of medication data is a radio frequency identification programming integrated with text.

10. The medication delivery system of claim 1 wherein the second label of patient data is a radio frequency identification programming integrated with text.

11. The medication delivery system of claim 1 wherein the means for reading the prescribed medication data, the medication delivery instruction, and patient data is selected from the group consisting of: bar code scanners, radio frequency identification readers, magnetic stripe or tape readers, and optical readers.

12. The medication delivery system of claim 1 wherein the means of reading the prescribed medication data, the medical delivery instruction, and the patient data of the handheld computing device is a two-dimensional bar code scanner.

13. The medication delivery system of claim 1 wherein the transmitter of the handheld computing device is an infrared transceiver.

14. The medication delivery system of claim 1 wherein the medical device is an electronic infusion pump.

15. The medication delivery system of claim 1 wherein the medication delivery device further has an adapter to facilitate the communication between the handheld computing device and the medication delivery device.

16. A medication delivery system comprising:
   (a) a container holding a medication, the container having a first bar code label in machine readable format containing medication data and a predetermined set of pump instructions for delivering the medication;
   (b) a tag adapted to be worn by a patient, the tag having a second bar code label in machine readable format containing patient data;
   (c) an infusion pump in communication with the medication container, the pump adapted to deliver the medication from the container to the patient via a catheter, the infusion pump having at least one delivery channel, and the pump having a data port for receiving information; and
   (d) a personal digital assistant having a bar code scanner thereon and a data transmitter thereon, the personal digital assistant configured to scan the first bar code label and the second bar code label and compare data from the scanned labels to confirm a match between the medication data and patient data, the personal digital assistant transmitter capable of transmitting the predetermined set of pumping instructions from the personal digital assistant to the infusion pump wherein the pump is adapted to deliver the medication to the patient according to the instructions.

17. The medication delivery system of claim 16 wherein in the container is an IV bag and the medication is an IV drug.

18. The medication delivery system of claim 16 wherein the tag containing patient data is a bracelet adapted to be worn by the patient.

19. The medication delivery system of claim 16 wherein the machine readable format of the first bar code is a two-dimensional bar code.

20. The medication delivery system of claim 16 wherein the machine readable format of the second bar code is a two-dimensional bar code.

21. The medication delivery system of claim 16 wherein the first label of medication data is a two-dimensional bar code integrated with text.

22. The medication delivery system of claim 16 wherein the second label of patient data is a two-dimensional bar code integrated with text.

23. The medication delivery system of claim 16 wherein the bar code scanner of the personal digital assistant is a two-dimensional bar code scanner.

24. The medication delivery system of claim 16 wherein the data transmitter on the personal digital assistant is an infrared transceiver and the data port on the pump for receiving information is an infrared transceiver.

25. The medication delivery system of claim 16 wherein the infusion pump further having an adapter to facilitate the communication between the personal digital assistant and the infusion pump.

26. The medication delivery system of claim 25 wherein the adapter of the infusion pump further providing infrared data communication between the infusion pump and the personal digital assistant.

27. The medication delivery system of claim 16 wherein the delivery channel of the infusion pump has a third label containing channel data identifying the channel, the channel data being in a machine readable format to be scanned by the bar code scanner of the personal digital assistant.

28. The medication delivery system of claim 16 wherein a pharmacy information system generates a print stream containing the medication data and the predetermined set of pump instructions for delivering the medication, and wherein the first bar code label is encoded with the data and instruction derived from the print stream.

29. A medication delivery system comprising:
   (a) a medication container containing a prescribed medication and a first label containing data on the prescribed medication, and instruction of delivering the prescribed medication, the medication data and medication delivery instruction being provided in machine readable format;
   (b) a tag adapted to be worn by a patient, the tag having a second label containing data on the patient, the patient data being provided in machine readable format;
   (c) a handheld computing device with:
      means for reading the prescribed medication data, the medication delivery instruction, and the patient data;
      means for storing the data; and
      means for communicating with other electronic devices; and
   (d) an electronic medication delivery device having the means for communicating with the handheld computing device to receive the medication delivery instruction from the handheld device to deliver the prescribed medication in the medication container to the patient via a catheter, the medication delivery device having at least one delivery channel;
   wherein the handheld computing device reads and stores the prescribed medication data and the patient data, performs a matching check between the prescribed medication data and the patient data to confirm a match, and communicates the medication delivery instruction to the electronic medication delivery device to deliver the medication to the patient.

30. The medication delivery system of claim 29 wherein the medication container is an IV bag, the prescribed medication is an IV drug.

31. The medication delivery system of claim 29 wherein the medication delivery device is an infusion pump.

32. The medication delivery system of claim 29 wherein the tag containing patient data is a bracelet adapted to be worn by the patient.

33. The medication delivery system of claim 29 wherein the machine readable data of the prescribed medication and the instruction of delivering the prescribed medication are coded in a format selected from the group consisting of: linear bar codes, two-dimensional bar codes, printed data encoding technology, radio frequency identification technology, magnetic stripes or tapes, optical character recognition technology, and optical holograms.

34. The medication delivery system of claim 29 wherein the machine readable prescribed medication data and medication delivery instruction are coded in two-dimensional bar codes.

35. The medication delivery system of claim 29 wherein the machine readable patient data is coded in a format selected from the group consisting of: linear bar codes, two-dimensional bar codes, printed data encoding technology, radio frequency identification technology, magnetic stripes or tapes, optical character recognition technology, and optical holograms.

36. The medication delivery system of claim 29 wherein the machine readable patient data is coded in two-dimensional bar codes.

37. The medication delivery system of claim 29 wherein the first label and the second label are generated by a software interface application that utilizes the print data stream from a pharmacy information system.

38. The medication delivery system of claim 29 wherein the means of reading the prescribed medication data, the medication delivery instruction, and the patient data of the handheld computing device is selected from the group consisting of: bar code scanners, radio frequency identification readers, magnetic stripe or tape readers, and optical readers.

39. The medication delivery system of claim 29 wherein the means of reading the prescribed medication data, the medical delivery instruction, and the patient data of the handheld computing device is a two-dimensional bar code scanner.

40. The medication delivery system of claim 29 wherein the first label containing medication data is a two-dimensional bar code with integrated text.

41. The medication delivery system of claim 29 wherein the second label containing patient data is a two-dimensional bar code with integrated text.

42. The medication delivery system of claim 29 wherein the first label containing medication data is a radio frequency identification programming with integrated text.

43. The medication delivery system of claim 29 wherein the second label containing patient data is a radio frequency identification with integrated text.

44. The medication delivery system of claim 29 wherein the means for communicating with other electronic devices is by infrared transmission.

45. The medication delivery system of claim 29 wherein the handheld computing device is a personal digital assistant.

46. The medication delivery system of claim 29 wherein the medication delivery device further comprising an adapter to facilitate the communication between the handheld computing device and the medication delivery device.

47. The medication delivery system of claim 46 wherein the adapter of the medication delivery device further providing infrared data communication between the medication delivery device and the handheld computing device.

48. The medication delivery system of claim 29 wherein the medication delivery device has multiple channels, each channel having a third label containing channel data identifying the channel, the channel data being in a machine readable format to be transmitted to the handheld computing device.

49. The medication delivery system of claim 29 wherein the catheter having a fourth label containing catheter data identifying the catheter, the catheter data being in a machine readable format to be transmitted to the handheld computing device.

50. A medication delivery system capable of communicating and matching prescribed medication data from a first label on a medication container holding the medication and patient data from a second label on a tag adapted to be worn by a patient wherein the first label also containing instruction of delivering the medication, and the data and instruction being provided in machine readable formats, the medication delivery system comprising:

(a) a handheld computing device with;
 means for reading the prescribed medication data, medication delivery instruction, and patient data;
 means for storing the data; and
 means for communicating with other electronic devices; and (b) an electronic medication delivery device to deliver the medication to the patient;

wherein the handheld computing device reads the prescribed medication data and the patient data, performs a matching check to confirm a match between the prescribed medication data and the patient data, and communicates the instruction of delivering the prescribed medication to the medication delivery device to deliver the medication to the patient.

51. The medication delivery system of claim 50 wherein the handheld computing device is a personal digital assistant.

52. The medication delivery system of claim 50 wherein the means for reading the prescribed medication data, the medication delivery instruction, and patient data is selected from the group consisting of: bar code scanners, radio frequency identification readers, magnetic stripe or tape readers, and optical readers.

53. The medication delivery system of claim 50 wherein the means of reading the prescribed medication data, the medical delivery instruction, and the patient data of the handheld computing device is a two-dimensional bar code scanner.

54. The medication delivery system of claim 50 wherein the means for communicating with other electronic devices is by infrared transmission.

55. The medication delivery system of claim 50 wherein the medication delivery device is an electronic infusion pump, the electronic infusion pump having at least one delivery channel.

56. The medication delivery system of claim 55 wherein the delivery channel of the electronic infusion pump having a third label containing channel data identifying the channel, the channel data being in a machine readable format to be transmitted to the handheld computing device.

57. The medication delivery system of claim 50 wherein the medication delivery device further having an adapter to facilitate the communication between the handheld computing device and the medication delivery device.

58. The medication delivery system of claim 57 wherein the adapter of the medication delivery device further providing infrared data communication between the medication delivery device and the handheld computing device.

* * * * *